US006489137B2

(12) United States Patent
Seeley

(10) Patent No.: US 6,489,137 B2
(45) Date of Patent: Dec. 3, 2002

(54) DETECTION OF LOSS OF THE WILD-TYPE HUBUB1 GENE

(75) Inventor: Todd W. Seeley, Moraga, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/095,881

(22) Filed: Jun. 11, 1998

(65) Prior Publication Data

US 2002/0123042 A1 Sep. 5, 2002

Related U.S. Application Data

(60) Provisional application No. 60/049,068, filed on Jun. 11, 1997, provisional application No. 60/068,102, filed on Dec. 19, 1997, and provisional application No. 60/070,182, filed on Dec. 30, 1997.

(51) Int. Cl.$^7$ .................. C07H 21/04; A01N 63/00; C12N 15/00; C12N 15/63; C12P 21/06
(52) U.S. Cl. .................. 435/69.1; 435/320.1; 435/455; 435/325; 536/23.1; 536/23.5
(58) Field of Search .................. 536/23.1, 23.5; 435/320.1, 325, 69.1, 455, 6; 424/93.2

(56) References Cited

U.S. PATENT DOCUMENTS

| 5,283,173 A | 2/1994 | Fields et al. ............ 435/6 |
| 5,518,911 A | 5/1996 | Abo et al. ............ 435/194 |

FOREIGN PATENT DOCUMENTS

| WO | WO 93/19752 | 10/1993 |
| WO | WO 96/09835 | 4/1996 |
| WO | WO 97/05157 | * 2/1997 |

OTHER PUBLICATIONS

Adams et al., EST Accession No. AA315653, Apr. 1997.*
Kerr et al., EST Accessin No. L26607, Mar. 1995.*
Hillier et al., EST Accession No. R94348, Aug. 1995.*
Taylor et al., GenEmbl Accession No. AF002823, Jun. 1997.*
Rudinger, Characteristics of the amino acids as components of a peptide hormone sequence, Jun. 1976, pp. 1–7.*
Hoyt et al., "S. cerevisiae Genes Required for Cell Cycle Arrest in Response to Loss of Microtubule Function" Cell 66:507–517, Aug. 9, 1991.
Taylor and McKeon, "Kinetochore Localization of Murine Bub1 is Required for Normal Mitotic Timing and Checkpoint Response to Spindle Damage" Cell 89:727–735, May 30, 1997.

Roberts et al., "The Saccharomyces cerevisiaeCheckpoint Gene Bub1 Encodes a Novel Protein Kinase" Molecular and Cellular Biology 14(12):8282–8281, Dec., 1994.
Pangilinan et al., "Mammalian Bub1 Protein Kinases: Map Positions and in Vivo Expression" Genomics 46:379–388, 1997.
Ouyang et al., "Human Bub1: A Putative Spindle Checkpoint Kinase Closely Linked to Cell Proliferation" Cell Growth and Differentation 9:877–885, Oct., 1998.
Hillier et al., "Washu–Merck Est Project 1997" May 25, 1997, Abstract No. XP–002084406.
Downs et al., "WD40–Repeat Type1 Transmembrane Protein A72.5" May 1, 1997, Abstract No. XP002084408.
Downs et al., "MUS Musculus WD40–Repeat Type I Transmembrane Protein A72.5 mRNA Complete CDS" Jan. 19, 1997, Abstract No. XP002084409.
Hillier et al., "WASHU–Merck Est Project 1997" May 25, 1997, Abstract No. XP002084407.
Database EMBL ID No. HS1249493, AC. No. AA449311, Jun. 10, 1997.
Database EMBL ID No. HS1229812, AC. No. AA430092, May 25, 1997.
Database EMBL ID No./AC. No. P97397, May 1, 1997.
Database EMBL ID No. MMU67327, AC. No. U67327, Jan. 19, 1997.
Hoyt et al., "S. cerevisiae Genes Required for Cell Cycle Arrest in Response to Loss of microtubule Function," Cell 66:507–517, 1991.
Ouyang et al., "Human Bub1: A Putative Spindle Checkpoint Kinase Closely Linked to Cell Proliferation," Cell Growth & Differentiation 9:877–885, 1998.
Roberts et al., "The Saccharomyces cerevisiae Checkpoint Gene BUB1 Encodes a Novel Protein Kinase," Molecular And Cellular Biology 14(12):8282–8290, 1994.
Taylor and McKeon, "Kinetochore Localization of Murine Bub1 Is Required for Normal Mitotic Timing and Checkpoint Response to Spindle Damage," Cell 89:727–735, 1997.

* cited by examiner

Primary Examiner—Scott D. Priebe
Assistant Examiner—Shin-Lin Chen
(74) Attorney, Agent, or Firm—Jane E. R. Potter; Kimberlin L. Morley; Robert P. Blackburn

(57) ABSTRACT

Methods are provided for assessing mutations and/or loss of the huBUB1 gene in human tumors. Loss of wild-type huBUB1 genes is involved in neoplastic development. Therapeutic regimens can be planned on the basis of the mutational status of huBUB1.

9 Claims, 2 Drawing Sheets

```
scBUB1-kinase  DLYCIRGELGEGGYATVYLAESS------QGHLRALKVEK---PASVWEYYIM
muBUB1-kinase  LVY-VNHLLGEGAFAQVFEAIHGDVRNAKSEQKCILKVQR---PANSWEFYIG
huBUB1-kinase  LVY-VHHLLGEGAFAQVYEATQGDLNDAKNKQKFVLKVQK---PANPWEFYIG
   pkc-kinase  TDFNFLMVLGKGSFGKVMLADRK-----GTEELYAIKILKKDVVIQD--DDVE
  rs6k-kinase  ECFELLRVLGKGGYGKVFQVRKVT--GANTGKIFAMKVLKKAMIVRN--AKDT
         cAPK  DQFERIKTLGTGSFGRVMLVKHKE-----TGNHYAMKILDKQKVVKL--KQIE
 GSK-3-kinase  VSYTDTKVIGNGSFGVVYQAKLCD-----SGELVAIKKVLQDKRFKNR----E
                   .  .* * . *                              .*
```

*Fig. 1*

DETECTION OF LOSS OF THE WILD-TYPE HUBUB1 GENE

This application claims the benefit of the following copending provisional applications: Serial No. 60/049,068, filed Jun. 11, 1997; Serial No. 60/068,102, filed Dec. 19, 1997; and Serial No. 60/070,182, filed Dec. 30, 1997. Each of these applications is incorporated by reference herein.

TECHNICAL AREA OF THE INVENTION

The invention relates to the area of cancer diagnostics. More particularly, the invention relates to detection of the loss and or alteration of wild-type huBUB1 genes in tumor tissues.

BACKGROUND OF THE INVENTION

Genes and proteins involved in cell cycle regulation and apoptosis have been found to be important in the development of cancers. There is a continuing need in the art for identification of components of cells which control the cell cycle and apoptosis.

SUMMARY OF THE INVENTION

The object of this invention is to provide tools and methods for diagnosing, prognosing, and treating neoplasia. This and other objects of the invention are provided by one or more of the embodiments described below.

One embodiment of the invention provides an isolated and purified huBUB1 protein comprising an amino acid sequence which is at least 85% identical to the amino acid sequence shown in SEQ ID NO:2.

Another embodiment of the invention provides an isolated and purified huBUB1 polypeptide which comprises at least 6 contiguous amino acids selected from an amino acid sequence which is at least 85% identical to the amino acid sequence shown in SEQ ID NO:2.

Yet another embodiment of the invention provides a fusion protein comprising a first protein segment and a second protein segment fused together with a peptide bond. The first protein segment comprises at least 6 contiguous amino acids of a huBUB1 protein having an amino acid sequence which is at least 85% identical to the amino acid sequence shown in SEQ ID NO:2.

Still another embodiment of the invention provides a preparation of antibodies which specifically binds to a huBUB1 protein.

Even another embodiment of the invention provides an isolated and purified subgenomic polynucleotide comprising at least 10 contiguous nucleotides selected from a nucleotide sequence which is at least 85% identical to the nucleotide sequence shown in SEQ ID NO:1.

A further embodiment of the invention provides a DNA expression construct comprising an isolated and purified subgenomic polynucleotide. The isolated and purified subgenomic polynucleotide comprises at least 10 contiguous nucleotides selected from a nucleotide sequence which is at least 85% identical to the nucleotide sequence shown in SEQ ID NO:1.

Another embodiment of the invention provides a host cell. The host cell comprises an isolated and purified subgenomic polynucleotide. The isolated and purified subgenomic polynucleotide comprises at least 10 contiguous nucleotides selected from a nucleotide sequence which is at least 85% identical to the nucleotide sequence shown in SEQ ID NO:1.

Still another embodiment of the invention provides a method of diagnosing a neoplastic tissue of a human. A tissue suspected of being neoplastic is isolated from a human. Loss of a wild-type huBUB1 gene or an expression product of a wild-type huBUB1 gene from the tissue is detected. The loss of the wild-type huBUB1 gene or its expression product indicates neoplasia of the tissue.

Yet another embodiment of the invention provides a method of supplying wild-type huBUB1 gene function to a cell which has lost said gene function by virtue of mutation in a huBUB1 gene. All or a portion of a wild-type huBUB1 gene is introduced into a cell which has lost said gene function. The portion of the wild-type huBUB1 gene is required for non-neoplastic growth of the cell. The all or a portion of the wild-type huBUB1 gene is expressed in the cell.

Even another embodiment of the invention provides a pair of single-stranded DNA primers. The pair of single-stranded DNA primers allows synthesis of all or part of a huBUB1 gene coding sequence.

Another embodiment of the invention provides a nucleic acid probe complementary to a wild-type huBUB1 gene as shown in SEQ ID NO:1.

Yet another embodiment of the invention provides a nucleic acid probe complementary to a mutant huBUB1 gene.

Still another embodiment of the invention provides a method of detecting the presence of a neoplastic tissue in a human. A body sample is isolated from a human. A mutant huBUB1 gene or expression product is detected in the body sample. Detection of a mutant huBUB1 gene or expression product indicates the presence of a neoplastic tissue in the human.

Another embodiment of the invention provides a method of detecting genetic predisposition to cancer in a human. A human sample selected from the group consisting of blood and fetal tissue is isolated. DNA is extracted from the sample. Loss of a wild-type huBUB1 gene from the DNA is detected. Detection of the loss of a wild-type huBUB1 gene indicates a genetic predisposition to cancer in the human.

A further embodiment of the invention provides a method for identifying test compounds which interfere with huBUB3-huBUB1 binding, said compounds being candidate therapeutic agents. A first protein, a second protein, and a test compound are contacted. The first protein comprises at least a portion of huBUB3 which binds to huBUB1 and the second protein comprises at least a portion of huBUB1 which binds to huBUB3 or the first protein comprises at least a portion of huBUB1 which binds to huBUB3 and the second protein comprises at least a portion of huBUB3 which binds to huBUB1. The quantity of the first protein which is bound to, is displaced from, or is prevented from binding to, the second protein or the quantity of the second protein which is bound to, displaced from, or is prevented from binding to the first protein is determined. A compound which diminishes the quantity of the first protein bound to the second protein or the second protein bound to the first protein, or which displaces the first protein bound to the second protein or the second protein bound to the first protein, or which prevents the first and second proteins from binding, is identified as a candidate therapeutic agent.

Another embodiment of the invention provides a method of identifying compounds which interfere with huBUB3-huBUB1 binding. A cell is contacted with a compound to be tested for its capacity to inhibit huBUB1-huBUB3 binding. The cell comprises a first fusion protein comprising a sequence-specific DNA-binding domain, a second fusion protein comprising a transcriptional activation domain, and a DNA construct comprising a reporter gene downstream from a DNA element which is recognized by the sequence-specific DNA binding-domain. The first fusion protein further comprises at least a portion of a huBUB3 protein which binds to a huBUB1 protein and the second fusion protein further comprises at least a portion of a huBUB1 protein which binds to a huBUB3 protein, or the first fusion protein further comprises at least a portion of a huBUB1 protein which binds to a huBUB3 protein and the second fusion protein further comprises at least a portion of a huBUB3 protein which binds to a huBUB1 protein. The amount of expression of the reporter gene in the presence of the compound is determined. A compound which decreases the amount of expression of the reporter gene is identified as a candidate therapeutic agent.

Still another embodiment of the invention provides a method of identifying test compounds which decrease the kinase activity of huBUB1. A huBUB1 protein is contacted with a test compound. The kinase activity of the huBUB1 protein is determined. A compound which decreases kinase activity of the huBUB1 protein is identified as a candidate therapeutic agent.

Even another embodiment of the invention provides a method of increasing the sensitivity of a tumor to an anti-tumor agent. The tumor is contacted with a compound which inhibits huBUB1 kinase activity or which inhibits huBUB1-huBUB3 binding. The sensitivity of the tumor to an anti-tumor agent is increased.

Another embodiment of the invention provides a method of expressing a huBUB1 subgenomic polynucleotide in a cell. The huBUB1 subgenomic polynucleotide is delivered to the cell. The huBUB1 subgenomic polynucleotide is expressed.

The present invention thus provides the art with the sequence of the human huBUB1 gene and protein. This information allows highly specific assays to be done to assess the neoplastic status of a particular tumor tissue.

BRIEF DESCRIPTION OF THE DRAWING

FIG. 1. FIG. 1 shows selected kinases, (SEQ ID NOS:9–15) including huBUB1 (SEQ ID NO:11), aligned using Clustal W.

FIG. 2 shows the chromosomal locations of the huBUB1 and huBUB3 genes.

DETAILED DESCRIPTION

Figure 2:
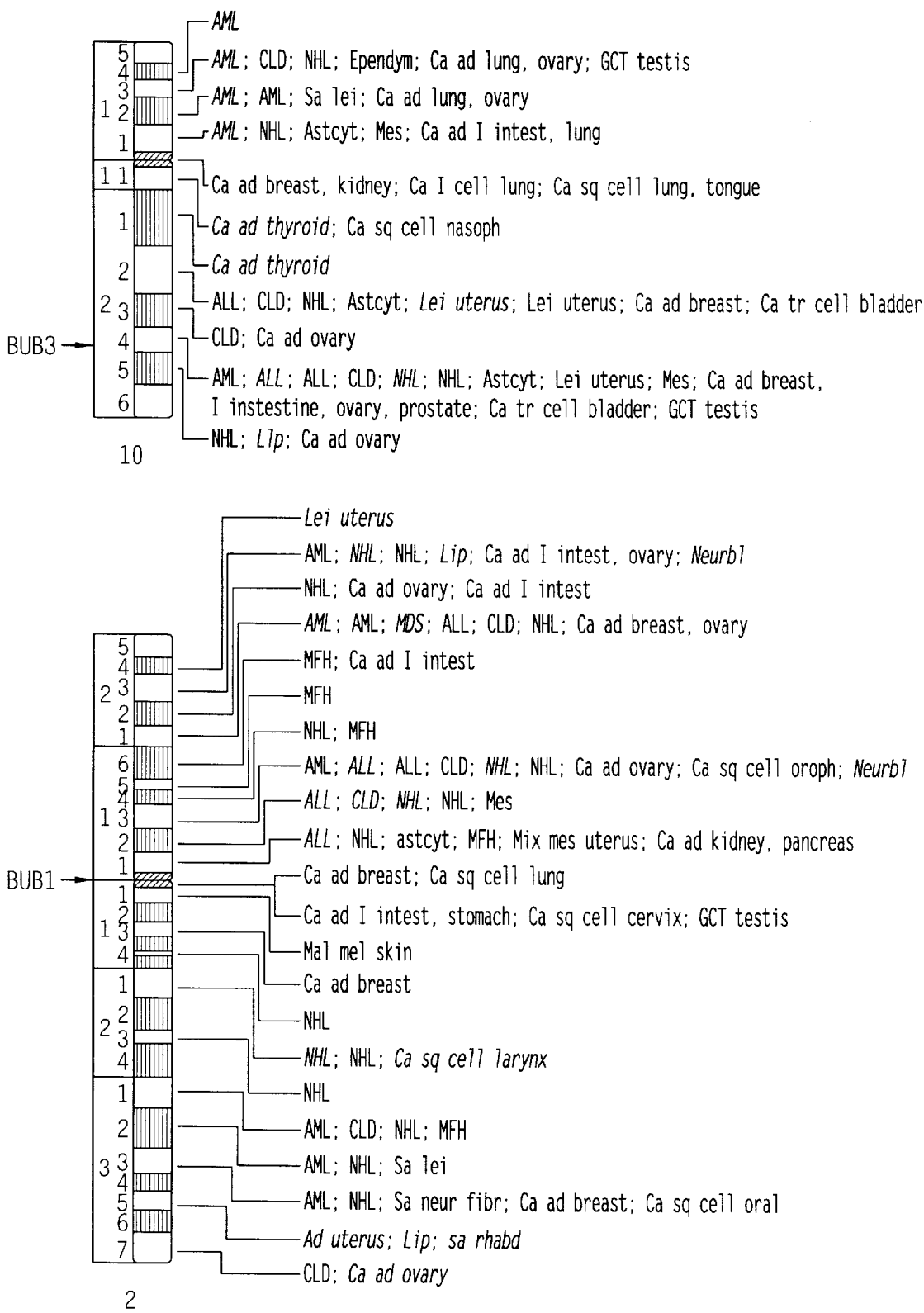
FIG. 2.

It is a discovery of the present invention that the human huBUB1 gene is involved in cell cycle control and apoptosis. A nucleotide sequence which encodes huBUB1 protein is shown in SEQ ID NO:1. huBUB1 protein binds to huBUB3 protein. The nucleotide and amino acid sequences of the huBUB3 gene and protein are shown in SEQ ID NOS:3 and 4, respectively. huBUB1 and the huBUB1-huBUB3 complex have kinase activity, and huBUB1 can autophosphorylate.

huBUB1 is mutated in cancer cells. Thus, loss of wild-type huBUB1 genes or function can be used to diagnose neoplasia. Furthermore, therapeutic regimens can be planned on the basis of the mutational status of huBUB1. Wild-type huBUB1 confers resistance to microtubule poisons such as vincristine, vinblastine, taxol, and taxotere. Thus, the finding of a mutation in huBUB1 will indicate that these agents can be used efficaciously. In contrast, finding a wild-type huBUB1 will suggest the use of other agents.

A huBUB1 protein has the amino acid sequence shown in SEQ ID NO:2. Any naturally occurring biologically active variants of this sequence which occur in human tissues are within the scope of this invention. Naturally occurring biologically active variants of full-length huBUB1 bind to huBUB3 and have kinase activity, including the ability to autophosphorylate. The huBUB3-binding domain of huBUB1 is located within amino acids 1–400 of SEQ ID NO:2, more particularly within amino acids 200–400 of SEQ ID NO:2. huBUB1 polypeptides differ in length from full-length huBUB1 and contain 6, 8, 10, 12, 15, 18, 20, 25, 30, 35, 40, 45, 50, 75, 80, 90, or 100 or more contiguous amino acids of a huBUB1 protein.

Variants of huBUB1 protein and huBUB1 polypeptides can also occur. huBUB1 variants can be naturally or non-naturally occurring. Naturally occurring huBUB1 variants are found in humans or other species and comprise amino acid sequences which are substantially identical to the amino acid sequence shown in SEQ ID NO:2. Non-naturally occurring huBUB1 variants which retain substantially the same biological activities as naturally occurring huBUB1 variants are also included here. Preferably, naturally or non-naturally occurring huBUB1 variants have amino acid sequences which are at least 85%, 90%, or 95% identical to amino acid sequences shown in SEQ ID NO:2 and have similar biological properties, such as kinase activity, including the ability to autophosphorylate, and the ability to bind to huBUB3. More preferably, the molecules are at least 98% or 99% identical. Percent sequence identity between a wild-type huBUB1 protein or polypeptide and a huBUB1 variant is calculated by counting the number of amino acid matches between the wild-type and the variant and dividing the total number of matches by the total number of amino acid residues of the wild-type huBUB1 sequence.

Preferably, amino acid changes in huBUB1 variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting huBUB1 variant. Properties and functions of huBUB1 variants are of the same type as a huBUB1 protein or polypeptide comprising amino acid sequences of SEQ ID NO:2, although the properties and functions of variants can differ in degree. Whether an amino acid change results in a functional huBUB1 variant can readily be determined. For example, binding of a huBUB1 variant to huBUB3 can be detected using specific antibodies, which are disclosed herein. Kinase activity of a huBUB1 variant itself or in a complex with huBUB3 can also be measured, as described below.

huBUB1 variants include glycosylated forms, aggregative conjugates with other molecules, and covalent conjugates with unrelated chemical moieties. huBUB1 variants also include allelic variants, species variants, and muteins. Truncations or deletions of regions which do not affect the binding of huBUB1 to huBUB3 or the kinase activity of huBUB1 are also huBUB1 variants. Covalent variants can be prepared by linking functionalities to groups which are found in the amino acid chain or at the N- or C-terminal residue, as is known in the art.

huBUB1 can be extracted, using standard biochemical methods, from huBUB1-producing human cells, such as spleen, thymus, prostate, testis, small intestine, colon, peripheral blood lymphocytes, heart, brain, placenta, lung, liver, skeletal muscle, kidney, or pancreas. An isolated and purified huBUB1 protein or polypeptide is separated from other compounds which normally associate with a huBUB1 protein or polypeptide in a cell, such as certain proteins, carbohydrates, lipids, or subcellular organelles. A preparation of isolated and purified huBUB1 proteins or polypeptides is at least 80% pure; preferably, the preparations are 90%, 95%, or 99% pure.

huBUB1 proteins and polypeptides can also be produced by recombinant DNA methods or by synthetic chemical methods. For production of recombinant huBUB1 proteins or polypeptides, coding sequences selected from the huBUB1 nucleotide sequence shown in SEQ ID NO:1, or variants of that sequence which encode huBUB1 protein, can be expressed in known prokaryotic or eukaryotic expression systems (see below). Bacterial, yeast, insect, or mammalian expression systems can be used, as is known in the art.

Alternatively, synthetic chemical methods, such as solid phase peptide synthesis, can be used to synthesize a huBUB1 protein or polypeptide. General means for the production of peptides, analogs or derivatives are outlined in Chemistry and Biochemistry of Amino Acids, Peptides, and Proteins—a Survey of Recent Developments, Weinstein, B. ed., Marcell Dekker, Inc., publ., New York (1983). Moreover, substitution of D-amino acids for the normal L-stereoisomer can be carried out to increase the half-life of the molecule. huBUB1 variants can be similarly produced.

Non-naturally occurring fusion proteins comprising at least 6, 8, 10, 12, 15, 18, 20, 25, 50, 60, 75, 80, 90, or 100 or more contiguous huBUB1 amino acids can also be constructed. huBUB1 fusion proteins are useful for generating antibodies against huBUB1 amino acid sequences and for use in various assay systems. For example, huBUB1 fusion proteins can be used to identify proteins which interact with huBUB1 protein and influence its kinase activity or which interfere with the binding of huBUB1 to huBUB3. Physical methods, such as protein affinity chromatography, or library-based assays for protein-protein interactions, such as the yeast two-hybrid or phage display systems, can also be used for this purpose. Such methods are well known in the art and can also be used as drug screens.

A huBUB1 fusion protein comprises two protein segments fused together by means of a peptide bond. The first protein segment comprises at least 6, 8, 10, 12, 15, 18, 20, 25, 30, 35, 40, 50, 60, 75, 80, 90, or 100 or more contiguous amino acids of a huBUB1 protein. For example, a huBUB1 fusion protein can comprise the huBUB3 binding site and/or the kinase domain of huBUB1. These domains can be recognized by aligning the amino acid sequence of huBUB1 with that of the yeast homolog, ScBUB1. The amino acids can be selected from the amino acid sequence shown in SEQ ID NO:2 or from a biologically active variant of that sequence, such as those described above. The first protein segment can also comprise full-length huBUB1.

The second protein segment can be a full-length protein or a protein fragment or polypeptide. The fusion protein can be labeled with a detectable marker, as is known in the art, such as a radioactive, fluorescent, chemiluminescent, or biotinylated marker. The second protein segment can be an enzyme which will generate a detectable product, such as β-galactosidase. The first protein segment can be N-terminal or C-terminal, as is convenient.

Techniques for making fusion proteins, either recombinantly or by covalently linking two protein segments, are also well known. Recombinant DNA methods can be used to prepare huBUB1 fusion proteins, for example, by making a DNA construct which comprises coding sequences selected from SEQ ID NO:1 in proper reading frame with nucleotides encoding the second protein segment and expressing the DNA construct in a host cell, as described below.

Isolated and purified huBUB1 proteins, polypeptides, variants, or fusion proteins can be used as immunogens, to obtain preparations of antibodies which specifically bind to huBUB1 protein. The antibodies can be used, inter alia, to detect wild-type huBUB1 protein or huBUB1-huBUB3 complexes in human tissue and fractions thereof The antibodies can also be used to detect the presence of mutations in the huBUB1 gene which result in under- or over-expression of a huBUB1 protein or in expression of a huBUB1 protein with altered size or electrophoretic mobility. Antibodies which specifically bind to huBUB3 protein can be similarly used and prepared, as described below for huBUB1 antibodies.

Preparations of polyclonal or monoclonal antibodies can be made using standard methods. Single-chain antibodies can also be prepared. Single-chain antibodies which specifically bind to huBUB1 proteins, polypeptides, variants, or fusion proteins can be isolated, for example, from single-chain immunoglobulin display libraries, as is known in the art. The library is "panned" against huBUB1 protein amino acid sequences, and a number of single chain antibodies which bind with high-affinity to different epitopes of huBUB1 protein can be isolated. Hayashi et al., 1995, Gene 160:129–30. Single-chain antibodies can also be constructed using a DNA amplification method, such as the polymerase chain reaction (PCR), using hybridoma cDNA as a template. Thirion et al., 1996, Eur. J. Cancer Prev. 5:507–11.

Single-chain antibodies can be mono- or bispecific, and can be bivalent or tetravalent. Construction of tetravalent, bispecific single-chain antibodies is taught in Coloma and Morrison, 1997, Nat. Biotechnol. 15:159–63. Construction of bivalent, bispecific single-chain antibodies is taught in Mallender and Voss, 1994, J. Biol. Chem. 269:199–206.

A nucleotide sequence encoding the single-chain antibody can be constructed using manual or automated nucleotide synthesis, cloned into DNA expression constructs using standard recombinant DNA methods, and introduced into cells which express the coding sequence, as described below. Alternatively, single-chain antibodies can be produced directly using, for example, filamentous phage technology. Verhaar et al., 1995, Int. J. Cancer 61:497–501; Nicholls et al., 1993, J. Immunol. Meth. 165:81–91.

huBUB1-specific antibodies specifically bind to epitopes present in a full-length huBUB1 protein having the amino acid sequence shown in SEQ ID NO:2, to huBUB1 polypeptides, or to huBUB1 variants, either alone or as part of a fusion protein. Preferably, huBUB1 epitopes are not present in other human proteins. Typically, at least 6, 8, 10, or 12 contiguous amino acids are required to form an epitope. However, epitopes which involve non-contiguous amino acids may require more, e.g., at least 15, 25, or 50 amino acids.

Antibodies which specifically bind to huBUB1 proteins, polypeptides, fusion proteins, or variants provide a detection signal at least 5-, 10-, or 20-fold higher than a detection signal provided with other proteins when used in Western blots or other immunochemical assays. Preferably, antibodies which specifically bind to huBUB1 epitopes do not detect other proteins in immunochemical assays and can immunoprecipitate a huBUB1 protein, polypeptide, fusion protein, or variant from solution.

Antibodies can be purified by methods well known in the art. Preferably, the antibodies are affinity purified, by passing the antibodies over a column to which a huBUB1 protein, polypeptide, variant, or fusion protein is bound. The bound antibodies can then be eluted from the column, for example, using a buffer with a high salt concentration.

Subgenomic polynucleotides contain less than a whole chromosome. Preferably, the polynucleotides are intron-free. Purified and isolated huBUB1 subgenomic polynucleotides can comprise at least 6, 8, 10, 12, 15, 20, 25, 30, 35, 40, 45, 50, 75, 100, 125, 150, 175, or 200 or more contiguous nucleotides selected from the nucleotide sequence shown in SEQ ID NO:1 or its complement. SEQ ID NO:1 is the coding sequence of a human huBUB1 gene. In one embodiment, a huBUB1 subgenomic polynucleotide comprises nucleotides which encode the kinase domain of huBUB1 or the huBUB3-binding site, as determined by aligning huBUB1 and ScBUB1 amino acid or nucleotide sequences.

The complement of the nucleotide sequence shown in SEQ ID NO:1 is a contiguous nucleotide sequence which forms Watson-Crick base pairs with the contiguous nucleotide sequence shown in SEQ ID NO:1. The complement of the nucleotide sequence shown in SEQ ID NO:1 (the antisense strand) is also a subgenomic polynucleotide, and can be used provide huBUB1 antisense oligonucleotides. huBUB1 subgenomic polynucleotides also include polynucleotides which encode huBUB1-specific single-chain antibodies and ribozymes, or fusion proteins comprising huBUB1 amino acid sequences.

Degenerate nucleotide sequences encoding amino acid sequences of huBUB1 protein and or variants, as well as homologous nucleotide sequences which are at least 85%, 90%, 95%, 98%, or 99% identical to the nucleotide sequence shown in SEQ ID NO:1, are also huBUB1 subgenomic polynucleotides. Percent sequence identity between the sequence of a wild-type huBUB1 subgenomic polynucleotide and a homologous huBUB1 nucleotide sequence is calculated by counting the number of nucleotide matches between the wild-type and the homolog and dividing the total number of matches by the total number of nucleotides of the wild-type huBUB1 sequence. Typically, homologous huBUB1 sequences can be confirmed by hybridization under stringent conditions, as is known in the art.

huBUB1 subgenomic polynucleotides can be isolated and purified free from other nucleotide sequences using standard nucleic acid purification techniques. For example, restriction enzymes and probes can be used to isolate polynucleotide fragments which comprise nucleotide sequences encoding a huBUB1 protein. Isolated and purified subgenomic polynucleotides are in preparations which are free or at least 90% free of other molecules.

Complementary DNA molecules which encode huBUB1 proteins can be made using reverse transcriptase, with huBUB1 mRNA as a template. The polymerase chain reaction (PCR) or other amplification techniques can be used to obtain hBUB1 subgenomic polynucleotides, using either human genomic DNA or cDNA as a template, as is known in the art. Alternatively, synthetic chemistry techniques can be used to synthesize huBUB1 subgenomic polynucleotides which comprise coding sequences for regions of huBUB1 proteins, single-chain antibodies, or ribozymes, or which comprise antisense oligonucleotides. The degeneracy of the genetic code allows alternate nucleotide sequences to be synthesized which will encode a huBUB1 protein comprising amino acid sequences of SEQ ID NO:2.

Purified and isolated huBUB1 subgenomic polynucleotides can be used as primers to obtain additional copies of the polynucleotides or as probes for identifying wild-type and mutant huBUB1 coding sequences. huBUB1 subgenomic polynucleotides can be used to express huBUB1 mRNA, protein, polypeptides, or fusion proteins and to generate huBUB1 antisense oligonucleotides and ribozymes.

A huBUB1 subgenomic polynucleotide comprising huBUB1 coding sequences can be used in an expression construct. Preferably, the huBUB1 subgenomic polynucleotide is inserted into an expression plasmid (for example, the Ecdyson system, pIND, In Vitro Gene). huBUB1 subgenomic polynucleotides can be propagated in vectors and cell lines using techniques well known in the art. huBUB1 subgenomic polynucleotides can be on linear or circular molecules. They can be on autonomously replicating molecules or on molecules without replication sequences. They can be regulated by their own or by other regulatory sequences, as are known in the art.

A host cell comprising a huBUB1 expression construct can then be used to express all or a portion of a huBUB1 protein. Host cells comprising huBUB1 expression constructs can be prokaryotic or eukaryotic. A variety of host cells are available for use in bacterial, yeast, insect, and human expression systems and can be used to express or to propagate huBUB1 expression constructs (see below). Expression constructs can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, and calcium phosphate-mediated transfection.

A huBUB1 expression construct comprises a promoter which is functional in a chosen host cell. The skilled artisan can readily select an appropriate promoter from the large number of cell type-specific promoters known and used in the art. The expression construct can also contain a transcription terminator which is functional in the host cell. The expression construct comprises a polynucleotide segment which encodes all or a portion of the huBUB1 protein, variant, fusion protein, antibody, or ribozyme. The polynucleotide segment is located downstream from the promoter. Transcription of the polynucleotide segment initiates at the promoter. The expression construct can be linear or circular and can contain sequences, if desired, for autonomous replication.

Bacterial systems for expressing huBUB1 expression constructs include those described in Chang et al., *Nature* (1978) 275: 615, Goeddel et al., *Nature* (1979) 281: 544, Goeddel et al., *Nucleic Acids Res.* (1980) 8: 4057, EP 36,776, U.S. Pat. No. 4,551,433, deBoer et al., *Proc. Natl. Acad Sci. USA* (1983) 80: 21–25, and Siebenlist et al., *Cell* (1980) 20: 269.

Expression systems in yeast include those described in Hinnen et al., *Proc. Natl. Acad Sci. USA* (1978) 75: 1929; Ito et al., *J. Bacteriol.* (1983) 153: 163; Kurtz et al., *Mol. Cell Biol.* (1986) 6: 142; Kunze et al., *J. Basic Microbiol.* (1985) 25: 141; Gleeson et al., *J. Gen. Microbiol.* (1986) 132: 3459, Roggenkamp et al., *Mol. Gen. Genet.* (1986) 202:302) Das et al., *J. Bacteriol.* (1984) 158: 1165; De Louvencourt et al., *J. Bacteriol.* (1983) 154: 737, Van den Berg et al., *Bio/Technology* (1990)8: 135; Kunze et al., *J. Basic Microbiol.* (1985)25:141; Cregg et al., *Mol. Cell. Biol.* (1985) 5: 3376, U.S. Pat. Nos. 4,837,148, 4,929,555; Beach and Nurse, *Nature* (1981) 300: 706; Davidow et al., *Curr. Genet.* (1985)10: 380, Gaillardin et al., *Curr. Genet.* (1985) 10: 49, Ballance et al., *Biochem. Biophys. Res. Commun.* (1983) 112: 284–289; Tilburn et al., *Gene* (1983)26: 205–221, Yelton et al., *Proc. Natl. Acad. Sci. USA* (1984) 81: 1470–1474, Kelly and Hynes, *EMBO J.* (1985) 4: 475479; EP 244,234, and WO 91/00357.

Expression of huBUB1 expression constructs in insects can be carried out as described in U.S. Pat. No. 4,745,051, Friesen et al. (1986) "The Regulation of Baculovirus Gene Expression" in: The Molecular Biology of Baculoviruses (W. Doerfler, ed.), EP 127,839, EP 155,476, and Vlak et al., *J. Gen. Virol.* (1988) 69: 765–776, Miller et al., *Ann. Rev. Microbiol.* (1988) 42: 177, Carbonell et al., *Gene* (1988) 73: 409, Maeda et al., *Nature* (1985) 315: 592–594, Lebacq-Verheyden et al., *Mol. Cell. Biol.* (1988) 8: 3129; Smith et al., *Proc. Natl. Acad. Sci. USA* (1985) 82: 8404, Miyajima et al., *Gene* (1987) 58: 273; and Martin et al., *DNA* (1988) 7:99. Numerous baculoviral strains and variants and corresponding permissive insect host cells from hosts are described in Luckow et al., *Bio/Technology* (1988) 6: 47–55, Miller et al., in Genetic Engineering (Setlow, J. K. et al. eds.), Vol. 8 Plenum Publishing, 1986), pp. 277–279, and Maeda et al., *Nature,* (1985) 315: 592–594.

Mammalian expression of huBUB1 expression constructs can be achieved as described in Dijkema et al., *EMBO J.* (1985) 4: 761, Gorman et al., *Proc. Natl. Acad Sci. USA* (1982b) 79: 6777, Boshart et al., *Cell* (1985) 41: 521 and U.S. Pat. No. 4,399,216. Other features of mammalian expression of huBUB1 expression constructs can be facilitated as described in Ham and Wallace, *Meth. Enz.* (1979) 58: 44, Barnes and Sato, *Anal. Biochem.* (1980) 102: 255, U.S. Pat. Nos. 4,767,704, 4,657,866, 4,927,762, 4,560,655, WO 90/103430, WO 87/00195, and U.S. Pat. No. RE 30,985.

Subgenomic polynucleotides of the invention can also be used in gene delivery vehicles, for the purpose of delivering a huBUB1 mRNA or oligonucleotide (either with the sequence of native huBUB1 mRNA or its complement), full-length huBUB1 protein, huBUB1 fusion protein, huBUB1 polypeptide, or huBUB1-specific ribozyme or single-chain antibody, into a cell preferably a eukaryotic cell. According to the present invention, a gene delivery vehicle can be, for example, naked plasmid DNA, a viral expression vector comprising a huBUB1 subgenomic polynucleotide, or a huBUB1 subgenomic polynucleotide in conjunction with a liposome or a condensing agent.

In one embodiment of the invention, the gene delivery vehicle comprises a promoter and a huBUB1 subgenomic polynucleotide. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter.

A huBUB1 gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the huBUB1 gene delivery vehicle is a recombinant retroviral vector. Recombinant retroviruses and various uses thereof have been described in numerous references including, for example, Mann et al., *Cell* 33:153, 1983, Cane and Mulligan, *Proc. Nat'l. Acad Sci. USA* 81:6349, 1984, Miller et al., *Human Gene Therapy* 1:5–14, 1990, U.S. Pat. Nos. 4,405,712, 4,861,719, and 4,980,289, and PCT Application Nos. WO 89/02,468, WO 89/05,349, and WO 90/02, 806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, *Cancer Res.* 53:3860–3864, 1993; Vile and Hart, *Cancer Res.* 53:962–967, 1993; Ram et al., *Cancer Res.* 53:83–88, 1993; Takamiya et al., *J. Neurosci. Res.* 33:493–503, 1992; Baba et al., *J. Neurosurg.* 79:729–735, 1993 (U.S. Pat. No. 4,777,127, GB 2,200,651, EP 0,345,242 and WO91/02805).

Particularly preferred retroviruses are derived from retroviruses which include avian leukosis virus (ATCC Nos. VR-535 and VR-247), bovine leukemia virus (VR-1315), murine leukemia virus (MLV), mink-cell focus-inducing virus (Koch et al., *J. Vir.* 49:828, 1984; and Oliffet al., *J. Vir.* 48:542, 1983), murine sarcoma virus (ATCC Nos. VR-844, 45010 and 45016), reticuloendotheliosis virus (ATCC Nos VR-994, VR-770 and 45011), Rous sarcoma virus, Mason-Pfizer monkey virus, baboon endogenous virus, endogenous feline retrovirus (e.g., RD114), and mouse or rat gL30 sequences used as a retroviral vector. Particularly preferred strains of MLV from which recombinant retroviruses can be generated include 4070A and 1504A (Hartley and Rowe, *J. Vir.* 19:19, 1976), Abelson (ATCC No. VR-999), Friend (ATCC No. VR-245), Graffi (Ru et al., *J. Vir.* 67:4722, 1993; and Yantchev *Neoplasma* 26:397, 1979), Gross (ATCC No. VR-590), Kirsten (Albino et al., *J. Exp. Med* 164:1710, 1986), Harvey sarcoma virus (Manly et al., *J. Vir.* 62:3540, 1988; and Albino et al., *J. Exp. Med* 164:1710, 1986) and Rauscher (ATCC No. VR-998), and Moloney MLV (ATCC No. VR-190). A particularly preferred non-mouse retrovirus is Rous sarcoma virus. Preferred Rous sarcoma viruses include Bratislava (Manly et al., *J. Vir.* 62:3540, 1988; and Albino et al., *J. Exp. Med.* 164:1710, 1986), Bryan high titer (e.g., ATCC Nos. VR-334, VR-657, VR-726, VR-659, and VR-728), Bryan standard (ATCC No. VR-140), Carr-Zilber (Adgighitov et al, *Neoplasma* 27:159, 1980), Engelbreth-Holm (Laurent et al., *Biochem Biophys Acta* 908:241, 1987), Harris, Prague (e.g., ATCC Nos. VR-772, and 45033), and Schmidt-Ruppin (e.g. ATCC Nos. VR-724, VR-725, VR-354) viruses.

Any of the above retroviruses can be readily utilized in order to assemble or construct retroviral huBUB1 gene delivery vehicles given the disclosure provided herein and standard recombinant techniques (e.g., Sambrook et al., *Molecular Cloning: A Laboratory Manual,* 2d ed., Cold Spring Harbor Laboratory Press, 1989, and Kunkle, *PNAS* 82:488, 1985) known in the art. Portions of retroviral huBUB1 expression vectors can be derived from different retroviruses. For example, retrovector LTRs can be derived from a murine sarcoma virus, a tRNA binding site from a Rous sarcoma virus, a packaging signal from a murine leukemia virus, and an origin of second strand synthesis from an avian leukosis virus. These recombinant retroviral vectors can be used to generate transduction competent retroviral vector particles by introducing them into appropriate packaging cell lines (see Ser. No. 07/800,921, filed Nov. 29, 1991, now abandoned). Recombinant retroviruses can be produced which direct the site-specific integration of the recombinant retroviral genome into specific regions of the host cell DNA. Such site-specific integration can be mediated by a chimeric integrase incorporated into the retroviral particle (see Ser. No. 08/445,466 filed May 22, 1995, now abandoned). It is preferable that the recombinant viral gene delivery vehicle is a replication-defective recombinant virus.

Packaging cell lines suitable for use with the above-described retroviral gene delivery vehicles can be readily prepared (see Ser. No. 08/240,030, filed May 9, 1994, now abandoned; see also WO 92/05266) and used to create producer cell lines (also termed vector cell lines or "VCLs") for production of recombinant viral particles. In particularly preferred embodiments of the present invention, packaging cell lines are made from human (e.g., HT1080 cells) or mink parent cell lines, thereby allowing production of recombinant retroviral gene delivery vehicles which are capable of surviving inactivation in human serum. The construction of recombinant retroviral gene delivery vehicles is described in detail in WO 91/02805. These recombinant retroviral gene delivery vehicles can be used to generate transduction competent retroviral particles by introducing them into appropriate packaging cell lines (see Ser. No. 07/800,921, now abandoned). Similarly, adenovirus gene delivery vehicles can also be readily prepared and utilized given the disclosure provided herein (see also Berkner, *Biotechniques* 6:616–627, 1988, and Rosenfeld et al., *Science* 252:431–434, 1991, WO 93/07283, WO 93/06223, and WO 93/07282).

A huBUB1 gene delivery vehicle can also be a recombinant adenoviral gene delivery vehicle. Such vehicles can be readily prepared and utilized given the disclosure provided herein (see Berkner, *Biotechniques* 6:616, 1988, and Rosenfeld et al., *Science* 252:431, 1991, WO 93/07283, WO 93/06223, and WO 93/07282). Adeno-associated viral huBUB1 gene delivery vehicles can also be constructed and used to deliver huBUB1 amino acids or nucleotides. The use of adeno-associated viral gene delivery vehicles in vitro is described in Chatterjee et al., *Science* 258: 1485–1488 (1992), Walsh et al., *Proc. Nat'l. Acad Sci.* 89: 7257–7261 (1992), Walsh et al., *J. Clin. Invest.* 94: 1440–1448 (1994), Flotte et al., *J. Biol. Chem.* 268: 3781–3790 (1993), Ponnazhagan et al., *J. Exp. Med.* 179: 733–738 (1994), Miller et al., *Proc. Nat'l Acad. Sci.* 91: 10183–10187 (1994), Einerhand et al., *Gene Ther.* 2: 336–343 (1995), Luo et al., *Exp. Hematol.* 23: 1261–1267 (1995), and Zhou et al., *Gene Therapy* 3: 223–229 (1996). In vivo use of these vehicles is described in Flotte et al., *Proc. Nat'l Acad. Sci.* 90: 10613–10617 (1993), and Kaplitt et al., *Nature Genet.* 8:148–153 (1994).

In another embodiment of the invention, a huBUB1 gene delivery vehicle is derived from a togavirus. Preferred togaviruses include alphaviruses, in particular those described in U.S. Ser. No. 08/405,627, filed Mar. 15, 1995, now abandoned WO 95/07994. Alpha viruses, including Sindbis and ELVS viruses can be gene delivery vehicles for huBUB1 polynucleotides. Alpha viruses are described in WO 94/21792, WO 92/10578 and WO 95/07994. Several different alphavirus gene delivery vehicle systems can be constructed and used to deliver huBUB1 subgenomic polynucleotides to a cell according to the present invention. Representative examples of such systems include those described in U.S. Pat. Nos. 5,091,309 and 5,217,879. Particularly preferred alphavirus gene delivery vehicles for use in the present invention include those which are described in WO 95/07994, and U.S. Ser. No. 08/405,627 now abandoned.

Preferably, the recombinant viral vehicle is a recombinant alphavirus viral vehicle based on a Sindbis virus. Sindbis constructs, as well as numerous simlar constructs, can be readily prepared essentially as described in U.S. Ser. No. 08/198,450. Sindbis viral gene delivery vehicles typically comprise a 5' sequence capable of initiating Sindbis virus transcription, a nucleotide sequence encoding Sindbis nonstructural proteins, a viral junction region inactivated so as to prevent subgenomic fragment transcription, and a Sindbis RNA polymerase recognition sequence. Optionally, the viral junction region can be modified so that subgenomic polynucleotide transcription is reduced, increased, or maintained. As will be appreciated by those in the art, corresponding regions from other alphaviruses can be used in place of those described above.

The viral junction region of an alphavirus-derived gene delivery vehicle can comprise a first viral junction region which has been inactivated in order to prevent transcription of the subgenomic polynucleotide and a second viral junction region which has been modified such that subgenomic polynucleotide transcription is reduced. An alphavirus-derived vehicle can also include a 5' promoter capable of initiating synthesis of viral RNA from cDNA and a 3' sequence which controls transcription termination.

Other recombinant togaviral gene delivery vehicles which can be utilized in the present invention include those derived from Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309 and 5,217,879 and in WO 92/10578. The Sindbis vehicles described above, as well as numerous similar constructs, can be readily prepared essentially as described in U.S. Ser. No. 08/198,450 now abandoned.

Other viral gene delivery vehicles suitable for use in the present invention include, for example, those derived from poliovirus (Evans et al., *Nature* 339:385, 1989, and Sabin et al., *J. Biol. Standardization* 1: 115, 1973) (ATCC VR-58); rhinovirus (Arnold et al., *J. Cell. Biochem.* L401, 1990) (ATCC VR-1110); pox viruses, such as canary pox virus or vaccinia virus Fisher-Hoch et al., *PNAS* 86:317, 1989; Flexner et al., *Ann. N.Y. Acad Sci.* 569:86, 1989; Flexner et al., *Vaccine* 8:17, 1990; U.S. Pat. Nos. 4,603,112 and 4,769,330; WO 89/01973) (ATCC VR-111; ATCC VR-2010); SV40 (Mulligan et al., *Nature* 277:108, 1979) (ATCC VR-305), (Madzak et al., *J. Gen. Vir.* 73:1533, 1992); influenza virus (Luytjes et al., *Cell* 59:1107, 1989; McMicheal et al., *The New England Journal of Medicine* 309:13, 1983; and Yap et al., *Nature* 273:238, 1978) (ATCC VR-797); parvovirus such as adeno-associated virus (Samulski et al., *J. Vir.* 63:3822, 1989, and Mendelson et al., *Virology* 166:154, 1988) (ATCC VR-645); herpes simplex virus (Kit et al., *Adv. Exp. Med. Biol.* 215:219, 1989) (ATCC VR-977; ATCC VR-260); *Nature* 277: 108, 1979); human immunodeficiency virus (EPO 386,882, Buchschacher et al., *J. Vir.* 66:2731, 1992); measles virus (EPO 440,219) (ATCC VR-24); A (ATCC VR-67; ATCC VR-1247), Aura (ATCC VR-368), Bebaru virus (ATCC VR-600; ATCC VR-1240), Cabassou (ATCC VR-922), Chikungunya virus (ATCC VR-64; ATCC VR-1241), Fort Morgan (ATCC VR-924), Getah virus (ATCC VR-369; ATCC VR-1243), Kyzylagach (ATCC VR-927), Mayaro (ATCC VR-66), Mucambo virus (ATCC VR-580; ATCC VR-1244), Ndumu (ATCC VR-371), Pixuna virus (ATCC VR-372; ATCC VR-1245), Tonate (ATCC VR-925), Triniti (ATCC VR-469), Una (ATCC VR-374), Whataroa (ATCC VR-926), Y-62-33 (ATCC VR-375), ONyong virus, Eastern encephalitis virus (ATCC VR-65; ATCC VR-1242), Western encephalitis virus (ATCC VR-70; ATCC VR-1251; ATCC VR-622; ATCC VR-1252), and coronavirus (Hamre et al., *Proc. Soc. Exp. Biol. Med.* 121:190, 1966) (ATCC VR-740).

A subgenomic huBUB1 polynucleotide of the invention can also be combined with a condensing agent to form a gene delivery vehicle. In a preferred embodiment, the condensing agent is a polycation, such as polylysine, polyarginine, polyornithine, protamine, spermine, spermidine, and putrescine. Many suitable methods for making such linkages are known in the art (see, for example, Ser. No. 08/366,787, filed Dec. 30, 1994 now abandoned).

In an alternative embodiment, a huBUB1 subgenomic polynucleotide is associated with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell which has internalized the liposome, thereby releasing its contents into the cytoplasm. Prior to interaction with the surface of a cell, however, the liposome membrane acts as a relatively impermeable barrier which sequesters and protects its contents, for example, from degradative enzymes. Additionally, because a liposome is a synthetic structure, specially designed liposomes can be produced which incorporate desirable features. See Stryer, *Biochemistry, pp.* 236–240, 1975 (W. H. Freeman, San Francisco, Calif.); Szoka et al., *Biochim. Biophys. Acta* 600:1, 1980; Bayer et al., *Biochim. Biophys. Acta.* 550:464, 1979; Rivnay et al., *Meth. Enzymol.* 149:119, 1987; Wang et al., *PNAS*84: 7851, 1987, Plant et al., *Anal. Biochem.* 176:420, 1989, and U.S. Pat. No. 4,762,915. Liposomes can encapsulate a variety of nucleic acid molecules including DNA, RNA, plasmids, and expression constructs comprising huBUB1 subgenomic polynucleotides such those disclosed in the present invention.

Liposomal preparations for use in the present invention include cationic (positively charged), anionic (negatively charged) and neutral preparations. Cationic liposomes have been shown to mediate intracellular delivery of plasmid DNA (Felgner et al., *Proc. Natl. Acad Sci. USA* 84:7413–7416, 1987), mRNA (Malone et al., *Proc. Natl. Acad Sci. USA* 86:6077–6081, 1989), and purified transcription factors (Debs et al., *J. Biol. Chem.* 265:10189–10192, 1990), in functional form. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. See also Felgner et al., *Proc. Natl. Acad Sci. USA* 91: 5148–5152.87, 1994. Other commercially available liposomes include Transfectace (DDAB/DOPE) and DOTAP/DOPE (Boerhinger). Other cationic liposomes can be prepared from readily available materials using techniques well known in the art. See, e.g. Szoka et al., *Proc. Natl. Acad. Sci. USA* 75:4194–4198, 1978; and WO 90/11092 for descriptions of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP staring materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., Methods of Immunology (1983), Vol. 101, pp. 512–527; Szoka et al., *Proc. Natl. Acad. Sci. USA* 87:3410–3414, 1990; Papahadjopoulos et al., *Biochim. Biophys. Acta* 394:483, 1975; Wilson et al., *Cell* 17:77, 1979; Deamer and Bangham, *Biochim. Biophys. Acta* 443:629, 1976; Ostro et al., *Biochem. Biophys. Res. Commun.* 76:836, 1977; Fraley et al., *Proc. Natl. Acad. Sci. USA* 76:3348, 1979; Enoch and Strittmatter, *Proc. Natl. Acad. Sci. USA* 76:145, 1979; Fraley et al., *J. Biol. Chem.* 255:10431, 1980; Szoka and Papahadjopoulos, *Proc. Natl. Acad. Sci. USA* 75:145, 1979; and Schaefer-Ridder et al., *Science* 215:166, 1982.

In addition, lipoproteins can be included with a huBUB1 subgenomic polynucleotide for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of polynucleotides to cells expressing lipoprotein receptors. Preferably, if lipoproteins are included with a polynucleotide, no other targeting ligand is included in the composition.

In another embodiment, naked huBUB1 subgenomic polynucleotide molecules are used as gene delivery vehicles, as described in WO 90/11092 and U.S. Pat. No. 5,580,859. Such gene delivery vehicles can be either huBUB1 DNA or RNA and, in certain embodiments, are linked to killed adenovirus. Curiel et al., *Hum. Gene. Ther.* 3:147–154, 1992. Other suitable vehicles include DNA-ligand (Wu et al., *J. Biol. Chem.* 264:16985–16987, 1989), lipid-DNA combinations (Felgner et al., *Proc. Natl. Acad. Sci. USA* 84:7413–7417, 1989), liposomes (Wang et al., *Proc. Natl. Acad. Sci.* 84:7851–7855, 1987) and microprojectiles (Williams et al., *Proc. Natl. Acad. Sci.* 88:2726–2730, 1991).

One can increase the efficiency of naked huBUB1 subgenomic polynucleotide uptake into cells by coating the polynucleotides onto biodegradable latex beads. This approach takes advantage of the observation that latex beads, when incubated with cells in culture, are efficiently transported and concentrated in the perinuclear region of the cells. The beads will then be transported into cells when injected into muscle. huBUB1 subgenomic polynucleotide-coated latex beads will be efficiently transported into cells after endocytosis is initiated by the latex beads and thus increase gene transfer and expression efficiency. This method can be improved further by treating the beads to increase their hydrophobicity, thereby facilitating the disruption of the endosome and release of huBUB1 subgenomic polynucleotides into the cytoplasm.

huBUB1 or huBUB3 activity can be decreased in a cell by contacting the cell with a reagent which binds to an expression product of huBUB1 or huBUB3, respectively. In one embodiment of the invention, the reagent is a ribozyme, an RNA molecule with catalytic activity. See, e.g., Cech, *Science* 236: 1532–1539; 1987; Cech, *Ann. Rev. Biochem.* 59:543–568; 1990, Cech, *Curr. Opin. Struct. Biol.* 2: 605–609; 1992, Couture and Stinchcomb, *Trends Genet.* 12: 510–515, 1996. Ribozymes can be used to inhibit gene function by cleaving an RNA sequence, as is known in the art (e.g., Haseloff et al., U.S. Pat. No. 5,641,673).

The coding sequence of a huBUB1 or huBUB3 genes can be used to generate ribozymes which will specifically bind to nRNA transcribed from the huBUB1 or huBUB3 genes. Methods of designing and constructing ribozymes which can cleave other RNA molecules in trans in a highly sequence specific manner have been developed and described in the art (see Haseloff, J. et al. *Nature* 334:585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach, et al., EP 321,201). The nucleotide sequences shown in SEQ ID NOS:1 and 3 provide a source of suitable hybridization region sequences. Longer complementary sequences can be used to increase the affinity of the hybridization sequence for the target. The hybridizing and cleavage regions of the ribozyme can be integrally related; thus, upon hybridizing to the target RNA through the complementary regions, the catalytic region of the ribozyme can cleave the target.

Ribozymes can be introduced into cells as part of a DNA construct, as is known in the art and described above. Mechanical methods, such as microinjection, liposome-mediated transfection, electroporation, or calcium phosphate precipitation, can be used to introduce the ribozyme-containing DNA construct into cells in which it is desired to decrease huBUB1 or huBUB3 expression, as described above. Alternatively, if it is desired that the cells stably retain the DNA construct, it can be supplied on a plasmid and maintained as a separate element or integrated into the genome of the cells, as is known in the art. The DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes can also be engineered to provide an additional level of regulation, so that destruction of mRNA occurs only when both a ribozyme and a target gene are induced in the cells.

In another embodiment of the invention, the level of huBUB1 or huBUB3 gene expression is decreased using an antisense oligonucleotide sequence. The antisense sequence is complementary to at least a portion of the sequence encoding huBUB1 or huBUB3 selected from the nucleotide sequences shown in SEQ ID NOS:1 or 3. Preferably, the antisense oligonucleotide sequence is at least 11 nucleotides in length, but can be at least 12, 15, 20, 25, 30, 35, 40, 45, or 50 or more nucleotides long. Longer sequences can also be used. Antisense oligonucleotide molecules can be provided in a DNA construct and introduced into cells as described above to decrease the level of huBUB1 or huBUB3 in the cells.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20:1–8, 1994; Sonveaux, *Meth. Mol. Biol.* 26:1–72, 1994; Uhlmann et al., *Chem. Rev.* 90:543–583, 1990.

Although precise complementarity is not required for successful duplex formation between an antisense molecule and the complementary coding sequence of a huBUB1 or huBUB3 gene, antisense molecules with no more than one mismatch are preferred. One skilled in the art can easily use the calculated melting point of an antisense-sense pair to determine the degree of mismatching which will be tolerated between a particular antisense oligonucleotide and a particular coding sequence.

Antisense oligonucleotides can be modified without affecting their ability to hybridize to a huBUB1 or huBUB3 coding sequence. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, can also be employed in a modified antisense oligonucleotide. These modified oligonucleotides can be prepared by methods well known in the art. See, e.g., Agrawal et al., *Trends Biotechnol.* 10:152–158, 1992; Uhlmann et al., *Chem. Rev.* 90:543–584, 1990; Uhlmann et al., *Tetrahedron. Lett.* 215:3539–3542, 1987.

Antibodies of the invention which specifically bind to huBUB1, particularly single-chain antibodies, can also be used to alter levels of huBUB1. Antibodies similarly prepared against huBUB3 can be used to alter levels of huBUB3. The antibodies prevent huBUB1 and huBUB3 from binding. Polynucleotides encoding single-chain antibodies of the invention can be introduced into cells as described above.

Preferably, the mechanism used to decrease the level of huBUB1 or huBUB3 expression, whether ribozyme, antisense oligonucleotide sequence, or antibody, decreases the level of gene expression by at least 50%, 60%, 70%, or 80%. Most preferably, the level of gene expression is decreased by at least 90%, 95%, 99%, or 100%. The effectiveness of the mechanism chosen to decrease the level of gene expression can be assessed using methods well known in the art, such as hybridization of nucleotide probes to huBUB1 or huBUB3 mRNA, quantitative RT-PCR, or detection of huBUB1 or huBUB3 protein using specific antibodies of the invention.

Compositions comprising huBUB1 or huBUB3 antibodies, ribozymes, or antisense oligonucleotides can optionally comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in huBUB1 or huBUB3 compositions, for example, mineral salts such as hydrochlorides, hydrobromides, phosphates, or sulfates, as well as salts of organic acids such as acetates, proprionates, malonates, or benzoates. huBUB1 or huBUB3 compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for a huBUB1 composition.

Typically, a huBUB1 or huBUB3 composition is prepared as an injectable, either as a liquid solution or suspension; however, solid forms suitable for solution or suspension in liquid vehicles prior to injection can also be prepared. A huBUB1 or huBUB3 composition can also be formulated into an enteric coated tablet or gel capsule according to known methods in the art, such as those described in U.S. Pat. No. 4,853,230, EP 225,189, AU 9,224,296, and AU 9,230,801.

Mutations in huBUB1 are diagnostic of neoplasia. According to a diagnostic method of the present invention, loss of the wild-type huBUB1 gene is detected. The loss may be due to either deletional and/or point mutational events. If only a single huBUB1 allele is mutated, an early neoplastic state may be indicated. However, if both alleles are mutated then a late neoplastic state may be indicated. Point mutational events may occur in regulatory regions, such as in the promoter of the huBUB1 gene, leading to loss or diminution of expression of the huBUB1 mRNA. This can be determined using assays for quantitating huBUB1 expression.

In order to detect the loss of the huBUB1 wild-type gene in a tissue, it is helpful to isolate the tissue free from surrounding normal tissues. Means for enriching a tissue preparation for tumor (or cancer) cells are known in the art. For example, the tissue may be isolated from paraffin or cryostat sections. Cancer cells may also be separated from normal cells by flow cytometry. These as well as other techniques for separating tumor from normal cells are well known in the art. If the tumor tissue is highly contaminated with normal cells, detection of mutations is more difficult.

Detection of point mutations may be accomplished by molecular cloning of the huBUB1 allele (or alleles) present in the tumor tissue and sequencing that allele(s) using techniques well known in the art. Alternatively, the polymerase chain reaction or other amplification techniques can be used to amplify huBUB1 gene sequences directly from a genomic DNA preparation from the tumor tissue. The DNA sequence of the amplified sequences can then be determined. The polymerase chain reaction itself is well known in the art. See, e.g., Saiki et al., *Science,* 239, 487, 1988; U.S. Pat. Nos. 4,683,203; and 4,683,195. Specific primers which can be used in order to amplify the huBUB1 gene will be discussed in more detail below.

Specific deletions of huBUB1 genes can also be detected. For example, restriction fragment length polymorphism (RFLP) probes for the huBUB1 gene or surrounding marker genes can be used to score loss of a huBUB1 allele. Other techniques for detecting deletions, as are known in the art can be used.

Loss of wild-type huBUB1 genes can also be detected on the basis of the loss of a wild-type expression product of the huBUB1 gene. Such expression products include both the mRNA as well as the huBUB1 protein product itself. Point mutations can be detected by sequencing the niRNA directly or via molecular cloning of cDNA made from the mRNA. The sequence of the cloned cDNA can be determined using DNA sequencing techniques which are well known in the art. The cDNA can also be sequenced via the polymerase chain reaction (PCR) which will be discussed in more detail below.

Alternatively, mismatch detection can be used to detect point mutations in the huBUB1 gene or its mRNA product. While these techniques are less sensitive than sequencing, they are simpler to perform on a large number of tumors. An example of a mismatch cleavage technique is the RNase protection method, which is described in detail in Winter et al., *Proc. Natl. Acad. Sci. U.S.A.* 82, 7575 (1985) and Meyers et al., *Science* 230, 1242 (1985). In the practice of the present invention the method involves the use of a labeled riboprobe which is complementary to the human wild-type huBUB1 gene. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the huBUB1 mRNA or DNA. The riboprobe need not be the full length of the huBUB1 mRNA or gene but can be a segment of either. If the riboprobe comprises only a segment of the huBUB1 mRNA or gene it will be desirable to use a number of these probes to screen the whole mRNA sequence for mismatches.

In similar fashion, DNA probes can be used to detect mismatches, through enzymatic or chemical cleavage. See, e.g., Cotton et al., *Proc. Natl. Acad. Sci. U.S.A.* 85, 4397 (1988) and Shenk et al., *Proc. Natl. Acad. Sci. U.S.A.* 72, 989 (1975). Alternatively, mismatches can be detected by shifts in the electrophoretic mobility of mismatched duplexes relative to matched duplexes. See, e.g., Cariello, *Human Genetics* 42, 726 (1988). With either riboprobes or DNA probes, the cellular mRNA or DNA which might contain a mutation can be amplified before hybridization using PCR or other amplification techniques, as is known in the art.

DNA sequences of the huBUB1 gene from the tumor tissue which have been amplified can also be screened using allele-specific probes. These probes are nucleic acid oligomers, each of which contains a region of the huBUB1 gene sequence harboring a known mutation. For example, one oligomer can be at least about 15, 18, 20, 30, or 50 nucleotides in length, corresponding to a portion of the huBUB1 gene sequence. By use of a battery of such allele-specific probes, amplification products can be screened to identify the presence of a previously identified mutation in the huBUB1 gene. Hybridization of allele-specific probes with amplified huBUB1 sequences can be performed, for example, on a nylon filter. Hybridization to a particular probe indicates the presence of the same mutation in the tumor tissue as in the allele-specific probe.

Loss of wild-type huBUB1 genes can also be detected by screening for loss of wild-type huBUB1 protein function. Although all of the functions which the huBUB1 protein undoubtedly possesses have yet to be elucidated, at least two specific functions are known. Protein huBUB1 binds to huBUB3. Loss of the ability of the huBUB1 protein to bind to huBUB3 indicates a mutational alteration in the protein which reflects a mutational alteration of the huBUB1 gene itself Similarly, loss of kinase activity of huBUB1 can be monitored as a means of detecting mutations. Alternatively, a panel of monoclonal or single-chain antibodies could be used in which epitopes involved in huBUB1 functions are represented by a monoclonal or single-chain antibody. Loss or perturbation of binding of huBUB1 to a monoclonal antibody in the panel would indicate mutational alteration of the huBUB1 protein and thus of the huBUB1 gene itself. Any means for detecting an altered huBUB1 protein can be used to detect loss of wild-type huBUB1 genes.

Mutant huBUB1 genes or gene products can also be detected in body samples, such as serum or stool, or other body fluids, such as urine and sputum. The same techniques discussed above for detection of mutant huBUB1 genes or gene products in tissues can be applied to other body samples. By screening such body samples, a simple early diagnosis can be achieved for many types of cancers. In addition, the progress of chemotherapy can be monitored more easily by testing such body samples for mutant huBUB1 genes or gene products.

The method of the present invention for diagnosis of neoplastic tissue is applicable across a broad range of tumors. These include lung, breast, brain, colorectal, bladder, mesenchyme, prostate, liver as well as stomach tumors. In addition, the method can be used in leukemias and osteosarcomas. It thus appears that the huBUB1 gene has a role in the development of a broad range of tumors. The methods of diagnosis of the present invention are applicable to any tumor in which huBUB1 has a role in tumorigenesis. The diagnostic method of the present invention is useful for clinicians so that they can decide upon an appropriate course of treatment. For example, a tumor displaying loss of wild-type huBUB1 alleles suggests the use of mitotic poison-type chemotherapy. Wild-type huBUB1 in a tumor suggests that other types of anti-cancer therapies should be used.

The invention also provides diagnostic kits. A kit of the present invention is useful for determination of the nucleotide sequence of a huBUB1 gene using the polymerase chain reaction or other amplification technique. A kit comprises one or a set of pairs of single-stranded DNA primers which can be annealed to sequences within or surrounding the huBUB1 gene in order to prime amplifying DNA synthesis of the huBUB1 gene itself. The complete set allows synthesis of all of the nucleotides of the huBUB1 gene coding sequences, although isolated primers for selected portions can also be used. The set of primers may or may not allow synthesis of both intron and exon sequences. However, it should allow synthesis of all exon sequences.

In order to facilitate subsequent cloning of amplified sequences, primers may have restriction enzyme sites appended to their 5' ends. Thus, all nucleotides of the primers are derived from huBUB1 sequences or sequences adjacent to huBUB1 except the few nucleotides necessary to form a restriction enzyme site. Such enzymes and sites are well known in the art. The primers themselves can be synthesized using techniques which are well known in the art. Generally, the primers can be made using synthesizing machines which are commercially available. In a preferred embodiment, the primer pairs comprise: TWS86 (5'ATCATTCATGGAGACATTAAGCC-3') (SEQ ID NO:5) and TWS87 (5'-TTTCATGTAAGAGCCAAAGAGCAT-3') (SEQ ID NO:6).

Nucleotide probes according to the present invention comprise at least about 10, 12, 14, 16, 18, 20, 25, or 30 contiguous nucleotides of huBUB1. They can also contain labeling moieties with which the probes can be detected, including but not limited to radiolabels, fluorescent labels, and enzymatic labels. Nucleotide probes provided by the present invention are useful in the RNase protection method, for detecting point mutations already discussed above. Probes can also be used to detect mismatches with a huBUB1 gene or mRNA using other techniques. Mismatches can be detected using other enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. See Cotton, supra; Shenk, supra; Myers, supra; Winter, supra; and Novack et al., *Proc. Natl. Acad. Sci. U.S.A.* 83, 586 (1986). If a riboprobe is used to detect mismatches with mRNA, it is complementary to the niRNA of the human wild-type huBUB1 gene. The riboprobe thus is an anti-sense probe in that it does not code for the huBUB1 protein because it is of the opposite polarity to the sense strand. The riboprobe generally will be radioactively labeled; such labeling can be accomplished by any means known in the art. If the riboprobe is used to detect mismatches with DNA it can be of either polarity, sense or anti-sense. Similarly, DNA probes also may be used to detect mismatches. Probes may also be complementary to mutant alleles of huBUB1. These probes are useful to detect similar mutations in other patients on the basis of hybridization rather than mismatches. These probes are discussed above and referred to as allele-specific probes.

Genetic predisposition to cancers or neoplasia can be ascertained by testing normal tissues of humans. For example, a person who has inherited a germline huBUB1 mutation would be prone to develop cancers. This predisposition can be deternined by testing DNA from any tissue of the person's body. Most simply, blood can be drawn and DNA extracted from cells of the blood. Loss of a wild-type huBUB1 allele, either by point mutation, deletion, or insertion can be detected by any of the means discussed above. DNA can also be extracted and tested from fetal tissues for this purpose.

According to the present invention a method is also provided of supplying wild-type huBUB1 function to a cell which carries mutant huBUB1 alleles. The wild-type huBUB1 gene or a part of the gene can be introduced into the cell in a vector such that the gene remains extrachromosomal. In such a situation the gene will be expressed by the cell from the extrachromosomal location. If a gene portion is introduced and expressed in a cell carrying a mutant huBUB1 allele, the gene portion should encode a part of the huBUB1 protein which is required for non-neoplastic growth of the cell. The portion of huBUB1 protein which is required for non-neoplastic growth can be readily determined, for example, by transfecting DNA expression constructs comprising portions of huBUB1 protein, such as the huBUB3 binding domain or the kinase domain, into neoplastic cell lines in vitro and observing alterations in cellular morphology or lowered rates of cell division, as is known in the art.

More preferred is the situation where the wild-type huBUB1 gene or a part of it is introduced into the mutant cell in such a way that it recombines with the endogenous mutant huBUB1 gene present in the cell. Such recombination would require a double recombination event which would result in the correction of the huBUB1 gene mutation. Vectors for introduction of genes both for recombination and for extra-chromosomal maintenance are known in the art and any suitable vector may be used.

A composition comprising all or a portion of a huBUB1 subgenomic polynucleotide or polypeptide or other molecule which has huBUB1 activity can be supplied to cells which carry mutant huBUB1 alleles. The active molecules can be introduced into the cells by local or systemic administration, including injection, oral administration, particle gun, or catheterized administration, and topical administration. Alternatively, some such active molecules can be taken up by the cells, actively or by diffusion.

Various methods can be used to administer a huBUB1 therapeutic composition directly to a specific site in the body. For treatment of a tumor, for example, an appropriate huBUB1 composition injected several times in several different locations within the body of the tumor. Alternatively, arteries which serve the tumor can be identified, and a huBUB1 composition can be injected into such an artery in order to deliver the composition to the tumor.

A tumor which has a necrotic center can be aspirated, and a huBUB1 composition can be injected directly into the now empty center of the tumor. A huBUB1 composition can also be administered directly to the surface of a tumor, for example, by topical application of the composition. X-ray imaging can be used to assist in certain of these delivery methods. Combination therapeutic agents, including a huBUB1 protein or polypeptide or a huBUB1 subgenomic polynucleotide, can be administered simultaneously or sequentially together with other therapeutic agents.

huBUB1 compositions can be delivered to specific tissues using receptor-mediated targeted delivery. Receptor-mediated DNA delivery techniques are taught in, for example, Findeis et al. *Trends in Biotechnol.* 11, 202–05, (1993); Chiou et al., Gene Therapeutics: Methods and Applications of Direct Gene Transfer (J. A. Wolff, ed.) (1994); Wu & Wu, *J. Biol. Chem.* 263,621–24,1988; Wu et al., *J. Biol. Chem.* 269, 54246, 1994; Zenke et al., *Proc. Natl. Acad Sci. U.S.A.* 87,3655–59,1990; Wu et al., *J. Biol Chem.* 266, 338–42,1991.

Both the dose of a particular huBUB1 composition and the means of administering the composition can be determined based on specific qualities of the huBUB1 composition, the condition, age, and weight of the patient, the progression of the particular disease being treated, and other relevant factors. If the composition contains huBUB1 proteins, polypeptides, or antibodies, effective dosages of the composition are in the range of about 5 $\mu$g to about 50 $\mu$g/kg of patient body weight, about 50 $\mu$g to about 5 mg/kg, about 100 $\mu$g to about 500 $\mu$g/kg of patient body weight, and about 200 to about 250 $\mu$g/kg.

Compositions containing huBUB1 subgenomic polynucleotides, including antisense oligonucleotides and ribozyme-or antibody-encoding sequences, can be administered in a range of about 100 ng to about 200 mg of DNA for local administration. Suitable concentrations range from about 500 ng to about 50 mg, about 1 $\mu$g to about 2 mg, about 5 $\mu$g to about 500 $\mu$g, and about 20 $\mu$g to about 100 $\mu$g of DNA. Factors such as method of action and efficacy of transformation and expression are considerations which will affect the dosage required for ultimate efficacy of the huBUB1 composition. If greater expression is desired over a larger area of tissue, larger amounts of a huBUB1 composition or the same amount administered successively, or several administrations to different adjacent or close tissue portions of, for example, a tumor site, may be required to effect a positive therapeutic outcome. In all cases, routine experimentation in clinical trials will determine specific ranges for optimal therapeutic effect.

Expression of an endogenous huBUB1 gene in a cell can be altered by introducing in frame with the endogenous huBUB1 gene a DNA construct comprising a huBUB1 targeting sequence, a regulatory sequence, an exon, and an unpaired splice donor site by homologous recombination, such that a homologously recombinant cell comprising a new huBUB1 transcription unit is formed. The new transcription unit can be used to turn the huBUB1 gene on or off as desired. This method of affecting endogenous gene expression is taught in U.S. Pat. No. 5,641,670, which is incorporated herein by reference.

The targeting sequence is a segment of at least 10, 12, 15, 20, or 50 contiguous nucleotides selected from the nucleotide sequence shown in SEQ ID NO:1. The transcription unit is located upstream of a coding sequence of the endogenous huBUB1 gene. The exogenous regulatory sequence directs transcription of the coding sequence of the huBUB1 gene.

The present invention also provides methods of screening test compounds for the ability to decrease or inhibit huBUB1 kinase activity or to interfere with huBUB1-huBUB3 binding. The test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art.

huBUB1 protein is a target for huBUB1 kinase activity in an autophosphorylation reaction. huBUB1-dependent phosphorylation is not be limited to huBUB1 protein, but can be successfully directed towards exogenous substrates. Thus, huBUB1 kinase activity can be employed in the development of screening assays directed at the identification of biochemical inhibitors of huBUB1. huBUB1 kinase inhibitors can be used to develop novel therapeutic approaches to cancer and other hyperproliferative disorders, such as psoriasis. Screening assays can employ other kinase substrates, such as truncated huBUB1 polypeptides, fusion proteins, synthetic peptides, or substrates unrelated to huBUB1. These alternative huBUB1 kinase substrates may have specific attributes (cost, ease of use, relative efficiency) which may make them preferable to the use of huBUB1 autophosphorylation as a means of monitoring kinase activity. Alternatively, knowledge of activity of a given protein as a huBUB1 kinase substrate has applications in the discovery of novel targets for diagnostic and/or therapeutic applications related to huBUB1. For example, a high-throughput filter-based library screening approach, which employs biochemical activity of specific known kinases to identify bacterial and/or phage clones expressing cloned substrates of kinase, can be used to identify biologically relevant sustrates of huBUB1 kinase. These cloned substrates can be characterized and employed in the further development of screening assays and/or pharmaceutical targets.

For example, compounds which decrease the kinase activity of huBUB1 or of a huBUB1-huBUB3 complex can be identified by contacting huBUB1 or a huBUB1-huBUB3 complex with a test compound and determining the kinase activity of the huBUB1 or huBUB1-huBUB3 complex. Any in vitro kinase assay known in the art, such as taught in W096/36642, can be used for this purpose (see also Example 7). Phosphorylation of a substrate, such as huBUB1 itself or a synthetic peptide substrate based on huBUB1 sequences shown in SEQ ID NO:2, or a kinase substrate such as PHAS-1, can be measured. Optionally, the substrate can comprise a detectable label, such as biotin, for use in a purification or separation step. A test compound which decreases kinase activity of huBUB1 or of the huBUB1-huBUB3 complex is identified as a candidate therapeutic agent.

Test compounds can also be screened for the ability to interfere with huBUB1-huBUB3 binding, in order to develop pharmaceuticals directed at inhibiting huBUB1 and/or huBUB3 function in cells. Such inhibitors can be, for example, polypeptides, small peptides, peptoids, or other peptide analogs or other chemical inhibitors. Some of these inhibitors, such as related peptides or fusion proteins, can be developed rationally on the basis of knowledge of the sequences of huBUB1 and huBUB3 which are disclosed herein. Alternatively, a random array of compounds can be screened for the ability to compete in a huBUB1-huBUB3 binding assay.

A test compound can be contacted with a mixture of huBUB3 protein and a contiguous sequence selected from the huBUB1 amino acid sequence shown in SEQ ID NO:2. These molecules can be produced recombinantly or can be synthesized using standard chemical methods. The proteins can be prebound prior to the step of contacting the test compound. Alternatively, the test compound can contact one of the proteins before the second protein is added.

The proteins can be in solution or one protein can be bound to a solid support. The proteins can be unlabeled or labeled, for example, with a radioactive, fluorescent, or other detectable marker. They can be fusion proteins comprising huBUB1 or huBUB3 fused to another protein with or without a detectable enzymatic activity.

In one embodiment, the amount of at least one of the two proteins that is bound or unbound in the presence of the test compound is then measured. A number of methods can be used to measure the amount of proteins or dimers. For example, the relative concentration of proteins bound to unbound can be detected by examining the apparent molecular masses of the molecules by size exclusion chromatography or by polyacrylamide gel electrophoresis under non-reducing conditions. Other methods of measuring binding or dissociation of the proteins will readily occur to those of ordinary skill in the art and can be used. A test compound which diminishes the quantity of the first protein bound to the second protein, or which displaces the first protein bound to the second protein, or which prevents the first protein from binding to the second protein is identified as a candidate therapeutic agent.

According to the present invention a method is also provided of using the yeast two-hybrid technique to screen for test compounds which interfere with huBUB1-huBUB3 binding. The yeast two-hybrid technique is generically taught in Fields, S. and Song, O., *Nature* 340, 245–46, 1989.

In a preferred embodiment, a cell is contacted with a test compound. The cell comprises two fusion proteins, which can be supplied to the cell by means of recombinant DNA constructs. The first fusion protein comprises a DNA-binding domain. The second fusion protein comprises a transcriptional activating domain. The first fusion protein also comprises either (i) at least a portion of huBUB1 that binds to huBUB3 or (ii) at least a portion of huBUB3 that binds to huBUB1. If the first fusion protein comprises at least the portion of huBUB1 that binds to huBUB3, then the second fusion protein comprises at least the portion of huBUB3 that binds to huBUB1. If the first fusion protein comprises at least the portion of huBUB3 that binds to huBUB1, then the second fusion protein comprises at least the portion of huBUB1 that binds to huBUB3. The cell also comprises a reporter gene comprising a DNA sequence downstream from a DNA element to which the DNA binding domain of the first fusion protein binds.

When the huBUB3 and huBUB1 regions are bound together, the DNA binding domain and the transcriptional activating domain will be in close enough proximity to reconstitute a transcriptional activator capable of initiating transcription of a detectable reporter gene in the cell. The expression of the reporter gene in the presence of the test compound is then measured. A test compound that increases the expression of the reporter gene is a potential drug for increasing huBUB1-huBUB3 binding. A test compound that decreases the expression of the reporter gene is a potential drug for decreasing huBUB1-huBUB3 binding.

Many DNA binding domains and transcriptional activating domains can be used in this system, including the DNA binding domains of GALA, LexA, and the human estrogen receptor paired with the acidic transcriptional activating domains of GAL4 or the herpes virus simplex protein VP16 (see, e.g., G. J. Hannon et al., *Genes Dev.* 7, 2378, 1993; A. S. Zervos et al., *Cell* 72, 223, 1993; A. B. Votjet et al., *Cell* 74, 205, 1993; J. W. Harper et al., *Cell* 75, 805, 1993; B. Le Douarin et al., *Nucl. Acids Res.* 23, 876, 1995). A number of plasmids known in the art can be constructed to contain the coding sequences for the fusion proteins using standard laboratory techniques for manipulating DNA (see, e.g., Example 1, below).

Suitable detectable reporter genes include the *E. coli* lacZ gene, whose expression can be measured calorimetrically (see, e.g., Fields and Song, supra), and yeast selectable genes such as HIS3 (Harper et al., supra; Votjet et al., supra; Hannon et al., supra) or URA3 (Le Douarin et al., supra). Methods for transforming cells are also well known in the art. See, e.g., A. Hinnen et al., *Proc. Natl. Acad. Sci. U.S.A.* 75, 1929–1933, 1978. The test compound can comprise part of the cell culture medium or it may be added separately.

The invention also provides methods of increasing the sensitivity of a tumor to a metabolic inhibitor. Normal cell division includes a highly controlled segregation of subcellular components, especially chromosomes and spindle pole bodies, a process which requires the function of microtubules. In normal cells, the presence of microtubule poisons arrests cell division prior to segregation of these components. In this manner, cells refrain from attempting to segregate these components under conditions which might affect the normal fidelity of this segregation.

In mutant cells lacking huBUB1 (and/or other genes known to function in this pathway such as huBUB3), a signal transduction pathway which senses proper microtubule function is absent. Thus, mutant cells treated with these drugs fail to regulate cell cycle progression. In this case, cell division occurs without proper segregation of subcellular components, and progeny cells may inherit a random fraction of genetic material (ranging from none to all), and may inherit one, none or both spindle poles. If progeny cells retain a less than complete complement of chromosomes and none or two spindle pole bodies, resulting cells are fated to die, either through loss of essential genes, through lack of spindle pole bodies, or through the catastrophic effects of a subsequent multipolar mitosis. This phenomenon is termed "mitotic catastrophe."

Mitotic catastrophe can be exploited to enhance the cytotoxic effect of anti-tumor agents on cancer cells to known microtubule poisons. Specifically, mutations in huBUB1 and functionally related genes (e.g., huBUB3) can determine the relative sensitivity of cells to microtubule poisons. In humans, the mutant status of huBUB1 and/or other genes can determine the relative cytotoxic effect of microtubule poison treatment in cancer chemotherapy. Such an effect may account for the difference between partial response and a complete remission in microtubule poison-mediated cancer chemotherapy. At the present time, the precise mechanism of tumor cytotoxicity by microtubule poisons in cancer chemotherapy is relatively poorly understood. Inactivation of huBUB1 and/or other genes can be used to increase the relative sensitivity of many tumors to microtubule poisons, such as vinblastin, taxol, vincristine, and taxotere. Treatment of tumors comprising huBUB1 mutant cells with these agents can induce gross failure of mitotic segregation of subcellular components, thereby producing profound cytotoxicity. In contrast, treatment of non-mutant cells can induce transient cell cycle delay, from which cells can immediately recover following termination of treatment. Thus, the mutational status of huBUB1 can be determined to indicate which chemotherapeutic regimes should be used. For example, since wild-type huBUB1 confers resistance to microtubule poisons, the finding of a mutation in huBUB1 in a tumor indicates that such agents could be employed effectively to treat the tumor. In contrast, finding a wild-type huBUB1 will suggest use of other agents.

The invention also provides a novel chemotherapeutic regimen for treating neoplasia or its symptoms, in which tumor cells with a wild-type copy of the huBUB1 gene can be induced to undergo a lethal mitotic catastrophe effect in the presence of microtubule inhibitors. This can be accomplished by administering one or more biochemical inhibitors of huBUB1 and/or huBUB3 function, as well as one or more microtubule poisons. Inhibitors of huBUB1 and/or huBUB3 generate a transient loss of huBUB1 function analogous to that seen in genetically huBUB1-mutant cells, thereby generating a failure to properly regulate cell cycle when confronted with a microtubule poison. The resulting cytotoxicity resulting from failure of mitotic segregation would parallel that seen in huBUB1 mutant cells, with the added benefit that upon removal of the huBUB1/huBUB3 inhibitor, cells would return to a genetically stable state. In this manner, a transient inhibition of this pathway can be used to exploit the normal requirement of loss of huBUB1 function for the chemotherapeutic efficacy of microtubule poisons.

huBUB1 or huBUB3 inhibitors can be identified, for example, by kinase screening assays or by interference with huBUB1-huBUB3 binding, as described herein. inhibitors can be added together, separately, or sequentially with the microtubule poison(s), as is desired. It is expected that the class of compounds including huBUB1/huBUB3 biochemical inhibitors described here would be used as adjuvants to normal cancer chemotherapy. Treated cells would therefore not be expected to express the constitutive genetic instability commonly observed in cancer cells. Cells transiently treated with huBUB1/huBUB3 inhibitors would be expected to return to a genetically stable state following cessation of treatment.

According to another aspect of the invention, potential drugs can be screened for utility as anti-cancer agents by the ability to suppress the expression or function of huBUB1 protein. Thus potential drugs can be contacted with cells and the expression of huBUB mRNA or protein monitored. This can be accomplished by well known techniques in the art, such as Northern blots, immunoprecipitation, immunoblots, etc. Any technique which utilizes a human huBUB1 nucleic acid probe or an antibody specific for human huBUB1 protein can be used. Other techniques, such as quantitative RT PCR can also be employed. In addition, in vitro techniques can be employed for testing the ability of candidate drugs to inhibit huBUB1 kinase activity or binding to huBUB3. Such assays are well within the skill of the art, once provided with the full sequence of the huBUB1 gene and protein. In addition, a yeast two-hybrid system can be used wherein one of the partners comprises all or a portion of huBUB1 and one of the partners comprises all or a portion of huBUB3. A cell which contains both of these partners can be contacted with test compounds and the loss or diminution of transactivation of the reporter gene can be monitored.

A huBUB1 subgenomic polynucleotide can also be delivered to subjects for the purpose of screening test compounds for those which are useful for enhancing transfer of huBUB1 subgenomic polynucleotides to the cell or for enhancing subsequent biological effects of huBUB1 subgenomic polynucleotides within the cell. Such biological effects include hybridization to complementary huBUB1 mRNA and inhibition of its translation, expression of a huBUB1 subgenomic polynucleotide to form huBUB1 mRNA and/or huBUB1 protein, and replication and integration of a huBUB1 subgenomic polynucleotide. The subject can be a cell culture or an animal, preferably a mammal, more preferably a human.

Test compounds which can be screened include any substances, whether natural products or synthetic, which can be administered to the subject. Libraries or mixtures of compounds can be tested. The compounds or substances can be those for which a pharmaceutical effect is previously known or unknown. The compounds or substances can be delivered before, after, or concomitantly with a huBUB1 subgenomic polynucleotide. They can be administered separately or in admixture with a huBUB1 subgenomic polynucleotide.

Integration of a delivered huBUB1 subgenomic polynucleotide can be monitored by any means known in the art. For example, Southern blotting of the delivered huBUB1 subgenomic polynucleotide can be performed. A change in the size of the fragments of a delivered polynucleotide indicates integration. Replication of a delivered polynucleotide can be monitored inter alia by detecting incorporation of labeled nucleotides combined with hybridization to a huBUB1 probe. Expression of a huBUB1 subgenomic polynucleotide can be monitored by detecting production of huBUB1 mRNA which hybridizes to the delivered polynucleotide or by detecting huBUB1 protein. huBUB1 protein can be detected immunologically. Thus, the delivery of huBUB1 subgenomic polynucleotides according to the present invention provides an excellent system for screening test compounds for their ability to enhance transfer of huBUB1 subgenomic polynucleotides to a cell, by enhancing delivery, integration, hybridization, expression, replication or integration in a cell in vitro or in an animal, preferably a mammal, more preferably a human.

The following examples are provided for exemplification purposes only and are not intended to limit the scope of the invention which has been described in broad terms above.

EXAMPLE 1

This Example demonstrates isolation of a human cDNA sequence encoding huBUB1.

A human cDNA sequence of huBUB1 was determined (see SEQ ID NO:1). The complete mRNA corresponding to this sequence was examined by Northern Blotting and found to be of ~3.5 kb in length. This mRNA is of sufficient length to encode a protein of ~1000 amino acids. The predicted translation product of the isolated cDNA includes a protein kinase domain. This human gene sequence is unique and no match has been identified to date using homology searches of human sequences in public databases.

EXAMPLE 2

This example demonstrates that huBUB1 is present in a complex with huBUB3.

Four plasmids based on the commercial vector pCR3.1 (Invitrogen) were constructed. These plasmids encode wild-type huBUB1 (p385-1), huBUB1 carrying a dinucleotide substitution in the kinase motif resulting in a lysine to alanine substitution of amino acid 821 (p403-1; see FIG. 1), wild type huBUB3 (p291-2), and an epitope tagged FLAG-huBUB3 variant protein (p221-2), which encodes three copies of the FLAG epitope followed by a glycine linker region fused in the proper reading frame to the 5' terminus of the huBUB3 ORF.

The region containing the glycine-rich ATP binding loop and active site lysine are depicted in FIG. 1. Conserved amino acid residues (*) and similar residues (.) are indicated. There are five candidate active site lysine residues in this region of the huBUB1 gene. Based on a comparison with murine and S. cerevisiae genes and on local amino acid context of these huBUB1 lysine residues, lysine 821 in the huBUB1 kinase motif (. . . VLKQV . . .) (SEQ ID NO:7) was targeted for site-directed mutagenesis using an overlapping PCR strategy. The AAA codon encoding lysine 821 was replaced by overlapping PCR with an AGC codon specifying alanine in the place of lysine. A mutant DNA fragment was then used to replace the corresponding fragment in p385-1. The resulting plasmid is referred to as p403-1.

The protein products of the genes encoded on these plasmids were then produced in vitro, using a commercial coupled transcription/translation kit (T7 TnT kit, Promega), either in the presence of $^{35}$S-labeled methionine (Amersham), or in reactions without radioactive label. Reaction mixtures of 15 µl included 150 ng of huBUB1 wild-type or mutant plasmid and 60 ng of huBUB3 or FLAG-huBUB3 plasmid. Other components were added as recommended by the manufacturer. Coupled transcription/translation reactions were allowed to proceed for two hours at 30° C. before addition of TNES buffer (50 mM Tris 7.5, 100 mM NaCl, 2 mM EDTA, 1% NP-40) to halt in vitro protein synthesis reactions. All buffers were supplemented with 1 mM DTT.

Aliquots of translation mixes were immunoprecipitated using anti-FLAG monoclonal antibody coupled to agarose beads (Kodak). Translation mixes were clarified by centrifugation and the soluble fraction was incubated 1 hour at room temperature with 9 µl immunobeads previously washed in binding buffer (TNES), in a final volume of 100 µl. Beads were collected by brief centrifugation, and were washed sequentially to remove unbound material. Beads were washed twice in binding buffer (TNES), twice in TNES lacking NP40 (TNE) supplemented with 2 M NaCl, and twice in TNE buffer lacking EDTA and supplemented with 10 mM $MgCl_2$.

Beads were collected by brief centrifugation. Beads were then resuspended in 10 µl SDS-PAGE sample buffer and heated briefly to 95° C. to release associated proteins. Eluates were loaded on 10–20% SDS-PAGE gels (Novex). Following electrophoresis for 1 hour at 200V, gels were fixed in Coomassie destain solution and dried onto Whatman 3 mm chromatography paper prior to autoradiographic analysis.

An aliquot of $^{35}$S-labeled reaction mixture was included on gels to indicate the relative efficiency of synthesis of the various plasmid products. Similar levels of labeled proteins were produced by the various plasmids used in these experiments. Following immunoprecipitation (IP) with anti-FLAG antibody beads, both FLAG-huBUB3 and huBUB1 material were retained by the beads. In IP pellets lacking FLAG-huBUB3, relatively small amounts of huBUB1 were consistently observed.

These results indicate association between FLAG-huBUB3 and huBUB1. Because weakly associated proteins would have been removed by the 2M NaCl washes, the retention of both huBUB1 and FLAG-BUB3 by anti-FLAG agarose beads likely indicates a high affinity interaction between these components. Low levels of huBUB1 precipitation in the absence of FLAG-BUB3 likely represents low level protein aggregation occurring late in the assay, as similar levels could be detected in mock immunoprecipitation reactions lacking anti-FLAG immunobeads. $^{35}$S-labeled huBUB1 lysine-821 to alanine mutant protein was also efficiently co-immunoprecipitated by FLAG-huBUB3, indicating that this amino acid is dispensable for huBUB1 interaction with FLAG-BUB3.

EXAMPLE 3

This example demonstrates autophosphorylation of huBUB1 and that lysine-821 is required for huBUB1 kinase activity.

Unlabeled in vitro transcription/translation reactions were prepared in parallel, immunoprecipitated, and further incubated with $^{33}$P-ATP kinase substrate. Washed beads from unlabeled transcription/translation reactions were collected and further incubated in final wash buffer (TNE buffer lacking EDTA and supplemented with 10 mM $MgCl_2$) supplemented with 10 nM $^{33}$P-abeled ATP (1 µCi per reaction), in a final volume of 25 µl. After 0.5 hr at room temperature, reactions were halted by addition of an excess of TNE buffer.

When wild-type huBUB1 was co-translated with FLAG-huBUB3, a $^{33}$P-labeled band with a relative migration in SDS-PAGE gels identical to that of huBUB1 was detected, suggesting that wild-type huBUB1 is a kinase substrate. Omission of FLAG-huBUB3 resulted in failure to detect significant $^{33}$P-labeled material. Because huBUB1 is poorly immuno-precipitated in the absence of FLAG-BUB3, this indicates that the labeled band represents huBUB1 translation product. Similarly, the absence of a huBUB1 band in reactions containing the huBUB1 lysine-821 to alanine mutant indicates failure of phosphorylation in this reaction.

This result indicates that the observed phosphorylation activity requires lysine-821 in the huBUB1 kinase motif. This result eliminates the possibility that the observed huBUB1 phosphorylation activity is due to a contaminating kinase co-immunoprecipitating with a FLAG-huBUB3/huBUB1 complex.

EXAMPLE 4

This example demonstrates the requirements for huBUB1 autophosphorylation activity.

Various experiments have been used to define the requirements of this autophosphorylation activity, including varying NaCi, $MgCl_2$, ATP, KCl, pH and time. The huBUB1 kinase is capable of autophosphorylation under a variety of conditions. Experiments have been conducted using an alternative immunoprecipitation protocol, in which an HA-epitope tag was introduced to the N-terminus of huBUB1, and complexes were precipitated using anti-HA monoclonal antibody and Protein G agarose beads (MB). HA-huBUB1 protein is also capable of autophosphorylation. Co-translation of huBUB3 may stimulate this autophosphorylation activity. This result may represent a biochemical activation of the kinase by huBUB3 association, or improved efficiency of huBUB1 folding by huBUB3 co-translation. Because similar results were obtained independently of the epitope tagging strategy, we conclude the affinity of huBUB1 for huBUB3 and the observed autophosphorylation activity of huBUB1 are not due to unrelated artefacts.

EXAMPLE 5

This example demonstrates the identification of potential huBUB1 auto-phoshorylation sites.

Small amounts of unlabeled in vitro synthesized huBUB1/FLAG-BUB3 material were produced in scaled-up reactions and purified by immunoprecipitation. huBUB1 was auto-phosphorylated in the presence of ATP. Proteins were eluted from beads by heating in SDS-PAGE sample buffer containing DTT, and separated on 10–20% SDS-PAGE gels (Novex). Gels were stained with Coomassie blue.

Faint huBUB1 and FLAG-huBUB3 bands could be identified by relative migration, and the band corresponding to huBUB1 was excised from the gel. Protein in this gel slice was degraded using trypsin and the resulting peptide fragments were analyzed by electrospray mass spectrophotometry.

Species with a fragmentation pattern consistent with the presence of leucine and/or isoleucine could be detected, some of which could be matched to the expected masses of huBUB1 tryptic fragments as predicted from huBUB1 DNA sequence data. Of these peptides, a subset with a fragmentation pattern suggesting the presence of phosphate could be identified, including a peptide corresponding to the predicted mass of the huBUB1 peptide RVITISK (amino acids SEQ ID NO:8 210–216 of SEQ ID NO:2). This peptide is tentatively identified as a site of huBUB1 autophosphorylation. huBUB1 protein sequence resembles known mixed function kinases, which may phosphorylate serine, threonine or tyrosine. The actual phosphorylated reside may therefore represent modification of either threonine 213 or serine 215 in the huBUB1 sequence, or may represent modification of both of these residues.

EXAMPLE 6

This example demonstrates a method of screening for inhibitors of huBUB1 kinase activity.

A set of known compounds was screened using an in vitro huBUB1 kinase assay. Tested compounds included olomucine, myrecetin, hypericin, iodotubercidin, ellagic acid, emodin, and staurosporine. The relative specificity of these compounds towards known kinases has been reported in the literature. Some of these compounds can be classified as relatively specific kinase inhibitors (e.g., olomucine, myrecetin, ellagic acid), while other inhibitors are known to inhibit a broad range of kinase (e.g., hypericin, iodotubercidin, staurosporine).

Unlabeled FLAG-BUB3/BUB1 in vitro translation products were immunopurified with anti-FLAG. $^{3}$P-ATP kinase reactions were performed in the presence and absence of inhibitors in 20 μl reaction volumes. Labeled reaction products were separated on SDS-PAGE gels, and relative huBUB1 autophosphorylation was determined with the aid of a phosphorimager. An initial screen was conducted using 10 and 20 μM of each compound. Compounds with a positive result in this screen were then retested at 5, 10 and 20 μM (Table 1).

TABLE I

| Dose | hypericin | iodotubercidin | staurosporine |
| --- | --- | --- | --- |
| 5 μM | 0.63 +/− 0.07 | 0.56 +/− 0.08 | 0.45 +/− 0.11 |
| 10 μM | 0.47 +/− 0.13 | 0.41 +/− 0.09 | 0.49 +/− 0.11 |
| 20 μM | 0.36 +/− 0.05 | 0.32 +/− 0.05 | 0.26 +/− 0.04 | huBUB1 kinase was clearly inhibited by hypericin, iodotubercidin, and staurosporine. These compounds fall in the class of compounds known as broad-range kinase inhibitors and are known inhibit a number of kinases at similar concentrations. These results demonstrate the successful use of screening assays directed towards the identification of biochemical inhibitors of the huBUB1 kinase.

EXAMPLE 7

This example demonstrates substrates of huBUB1 kinase.

Immunopurified FLAG-BUB3/BUB1 $^{33}$P-ATP kinase reactions were assembled as described with the addition of 1 μg of potential kinase substrate per 20 μl kinase reaction. Parallel reactions in which huBUB1 was replaced with the previously described huBUB1-K821A mutant were also run. Reaction products were then separated on SDS-PAGE gels and visualized by autoradiography.

Tested protein targets included PHAS-I (Strategene), casein, myelin basic protein (MBP), histone HI, and GST-p53 protein. Of these, only PHAS-I demonstrated clear huBUB1-dependent activity as a kinase substrate. Reactions containing the huBUB1-K821A mutant protein failed to produce labeled products, indicating that phosphorylation of PHAS-I requires huBUB1 activity.

These results demonstrate the utility of exogenous substrates in the determination of huBUB1 kinase activity. This result also demonstrates that a small scale screen can be directed at the identification of huBUB1 protein substrates, with potential applications towards the discovery of novel targets for novel diagnostic and therapeutic applications related to huBUB1.

PHAS-I substrate did not appear to interfere with the huBUB1 autophosphorylation reaction. This may indicate that the huBUB1 autophosphorylation reaction is more efficient than PHAS-I phosphorylation. This could occur if huBUB1 autophosphorylation occurs in a relatively efficient unimolecular reaction, through the phosphorylation of an individual monomer by the kinase domain of the same monomer. Alternatively, huBUB1 autophosphorylation could occur between separate huBUB1 monomers, in which case a freely associating exogenous substrate might be expected to more efficiently complete for huBUB1 phosphorylation.

EXAMPLE 8

This example demonstrates a small-scale screen to identify proteins and polypeptides which associate with or bind to huBUB1 and/or huBUB3. This screen can easily be adapted to identify small molecule inhibitors of huBUB1-huBUB3 binding, which could provide novel pharmaceuticals directed against huBUB1 and/or huBUB3 function. Using this assay, we define a subdomain of the N-terminus of huBUB1 as sufficient for huBUB3 association. This domain can serve as a useful source of peptide sequence with potential inhibitory properties in a huBUB1-huBUB3 interaction assay.

A number of huBUB1-encoding plasmids were produced. Plasmid p385-1, encoding full-length huBUB1 in the vector pCR3.1 (Invitrogen), was employed as a backbone for further constructs. All constructs were in the proper orientation to be transcribed and translated in coupled reactions using the bacteriophage T7 promoter site located immediately upstream of the cloning site in vector pCR3.1. A full-length HA-epitope tagged huBUB1 plasmid was constructed (p396-1), which encodes a triple HA tag followed by a 6×glycine linker fused to the huBUB1 ATG start site. C-terminal truncation variants of this plasmid were also produced, including a construct encoding HA-BUB1 1–199 (p365-2), representing a deletion of the C terminus to an internal huBUB1 EcoRV site; HA-BUB1 1–400 (p377-2), representing a N-terminal MiuNI huBUB1 fragment; and HA-BUB1 200–400 (p365-1), which fuses the HA tag to an internal EcoRVMuNI BUB1 fragment. These truncation variants include additional vector-encoded peptide sequences at their C-termini. Additional constructs used in the studies described here include pCR3.1-based human MAD2 and hu-rae1 expression plasmids (designated p344-6 and p375-1, respectively) produced by cloning PCR products derived from the open reading frames (ORFs) for these genes, as described in their respective Genbank entries (for human MAD2, HSRNAMAD and HSU65410; for hu-rae1, HSU84720).

$^{35}$S-methionine-labeled proteins and polypeptides were then produced from these plasmids by coupled in vitro transcription/translation reactions (IVT), as described above. IVT reactions were immunoprecipitated (IP), using either anti-FLAG agarose beads (Kodak IBI) or anti-HA monoclonal antibody combined with Protein G beads (BMB). Beads were extensively washed as previously described to ensure the removal of non-specifically-associated proteins, including relatively stringent washes in 2 M NaCl buffer. Bound proteins were released from beads by heating samples in SDS-sample buffer and were analyzed on 10–20% SDS-PAGE gels. Aliquots of initial $^{35}$S-labeled translation reactions were analyzed as well.

Polypeptides observed to associate with FLAG-BUB3 included full-length huBUB1, as well as huBUB1 truncation variants HA-BUB1 200–400 and HA-BUB1 1–400. Proteins not retained by FLAG-BUB3 included human MAD2, untagged huBUB3, and HA-BUB1 1–199.

A second set of experiments was used to demonstrate affinity of various polypeptides for HA-BUB1 1–400. Both huBUB3 and FLAG-BUB3 bound to HA-BUB1 1–400. Neither full-length huBUB1 or the product of the human rael gene were observed to associate with this domain of huBUB1.

The association of truncation variants of huBUB1 with FLAG-BUB3 under these relatively stringent conditions suggests that an N-terminal subdomain of huBUB1 encompassed by the HA-BUB1 200–400 truncation variant is sufficient for recognizing huBUB3. Similar results were obtained when the HA-BUB1 1–400 truncation variant was used independently to immunoprecipitate huBUB3 and FLAG-BUB3, demonstrating that these protein-protein interactions can be observed independently from the IP method.

Omission of the 2 M NaCl IP washes allowed the detection of some retention of HA-BUB1 1–199 by FLAG-BUB3. The observation of relatively weak association of FLAG-BUB3 with HA-BUB1 1–199 vs. HA-BUB1 200–400 was somewhat surprising. Alignment of S. cerevisiae and huBUB1 sequences suggested that a domain in the first 200 amino acids of huBUB1 retains the most highly conserved segments of amino acid sequences between these proteins, defining a conserved domain that we initially presumed would be sufficient to mediate high affinity huBUB3 interaction. A relatively weakly conserved second huBUB1 homolog has been described (huBUB1R1; Cahill et al., Nature 392:300–303), and a second domain of additional amino acid sequence homology between huBUB1 and huBUB1R1 was identified near the N-terminus, corresponding to sequences retained in the HA-BUB1 200–400 construct. We conclude that a domain in this region of huBUB1 is sufficient for high affinity huBUB1-huBUB3 association, but that additional protein-protein contacts are likely made by a domain present in the HA-BUB1 1–199 construct.

While huBUB3 clearly associates with huBUB1, huBUB3 was excluded from huBUB1-FLAG-BUB3 anti-FLAGIP complexes. This result suggests that huBUB1 complexes retain a single huBUB3 monomer and that huBUB3 does not freely self-associate. When huBUB3 was present, the yield of huBUB1 in FLAG-BUB3 complexes was reduced. This result was reproducibly obtained and indicates competition between FLAG-BUB3 and huBUB3 in the translation mix for association with huBUB1.

HA-BUB1 1–400 fails to associate with full-length huBUB1 in the presence of BUB3. Other experiments using full-length HA-BUB1 indicated that untagged huBUB1 was similarly excluded from HA-BUB1/BUB3 anti-HA IP complexes. These results suggest in turn that huBUB3 complexes retain a single huBUB1 monomer, and that huBUB1 does not freely self-associate. Accordingly, we conclude that the huBUB1-huBUB3 complexes studied in these experiments consist of a single monomer of each protein.

The association of hu-rael translation product with the huBUB3 binding domain of huBUB1 was also investigated. Homology searches identified both the huBUB3 and hu-rael proteins as candidate ligands for huBUB1, based on the fact that both proteins express significant homology to S. cerevisiae BUB3. We have not identified conditions which allow significant association to be detected between the hu-rael protein and huBUB1. Both hu-rae-1 and huBUB3 consist almost exclusively of WD40 (trp-asp) repeat motifs. Hu-rae-1 is also structurally related to the S. pombe rael gene and the S. cerevisiae YET7 gene, which have not been reported to play roles in signaling kinetochore function.

We also studied the association of the human MAD2 gene product with huBUB1 and huBUB3. Murine BUB1 and human MAD2 have each been shown to associate with human kinetochores. huBUB1 and huBUB3 are localized to mitotic nuclei in overexpressing cells. Strong homology to S. cerevisiae MAD2 suggests that the human MAD2 homolog functions in the same regulatory pathway. We have not identified conditions where a clear complex of human MAD2 and huBUB1 or huBUB3 proteins can be observed. At this point, we cannot rule out that MAD2 associates with huBUB1 and/or huBUB3 under some other conditions, either directly or in the form of a tertiary complex with other unknown proteins.

What is claimed is:

1. An isolated and purified subgenomic polynucleotide consisting essentially of a nucleotide sequence shown in SEQ ID NO: 1.

2. A DNA expression construct comprising an isolated and purified subgenomic polynucleotide consisting essentially of a nucleotide sequence shown in SEQ ID NO:1.

3. A host cell comprising an isolated and purified subgenomic polynucleotide consisting essentially of a nucleotide sequence shown in SEQ ID NO:1.

4. A method of expressing a huBUB1 subgenomic polynucleotide in a cell in vitro, comprising the step of:
   delivering a huBUB1 subgenomic polynucleotide having a nucleotide sequence shown in SEQ ID NO:1 to the cell, wherein said polynucleotide sequence contains a complete open reading frame, whereby the huBUB1 subgenomic polynucleotide is expressed.

5. An isolated and purified subgenomic polynucleotide encoding a mutant huBUB1 polypeptide, consisting essentially of the nucleotide sequence shown in SEQ ID No. 1 except said polynucleotide contains a mutation and encodes a mutant huBUB1 polypeptide containing a mutation of the amino acid lysine at position 821 of SEQ ID No. 2, and wherein the mutant huBUB1 polypeptide contains an alanine at amino acid position 821 of SEQ ID No. 2.

6. An isolated oligonucleotide probe consisting essentially of at least 10 nucleotides complementary to a huBUB1 nucleic acid sequence to detect a mutation of huBUB1 at amino acid position 821 of SEQ ID NO:2.

7. A polynucleotide which encodes a mutant huBUB1 protein comprising an amino acid sequence of SEQ ID NO:2 except the encoded mutant huBUB1 protein contains an alanine at position 821 of SEQ ID NO:2.

8. A host cell comprising a construct which comprises a promoter; and the polynucleotide of claim 7.

9. A construct comprising:

a promoter; and a polynucleotide segment encoding a mutant huBUB1 protein comprising an amino acid sequence of SEQ ID NO:2 except the encoded mutant huBUB1 protein contains an alanine at position 821 of SEQ ID NO:2 wherein the polynucleotide segment is located downstream from the promoter, wherein transcription of the polynucleotide segment initiates at the promoter.

* * * * *

SEQUENCE LISTING

<160> NUMBER OF SEQ ID NOS: 15

<210> SEQ ID NO 1
<211> LENGTH: 3441
<212> TYPE: DNA
<213> ORGANISM: Homo sapien

<400> SEQUENCE: 1

| | | | | | |
|---|---|---|---|---|---|
| caggtttggc | cgctgccggc | cagcgtcctc | tggccatgga | caccccggaa | aatgtccttc | 60 |
| agatgcttga | agcccacatg | cagagctaca | agggcaatga | ccctcttggt | gaatgggaaa | 120 |
| gatacataca | gtgggtagaa | gagaattttc | ctgagaataa | agaatacttg | ataactttac | 180 |
| tagaacattt | aatgaaggaa | tttttagata | agaagaaata | ccacaatgac | ccaagattca | 240 |
| tcagttattg | tttaaaattt | gctgagtaca | acagtgacct | ccatcaattt | tttgagtttc | 300 |
| tgtacaacca | tgggattgga | accctgtcat | cccctctgta | cattgcctgg | gcggggcatc | 360 |
| tggaagccca | aggagagctg | cagcatgcca | gtgctgtcct | tcagagagga | attcaaaacc | 420 |
| aggctgaacc | cagagagttc | ctgcaacaac | aatacaggtt | atttcagaca | cgcctcactg | 480 |
| aaacccattt | gccagctcaa | gctagaacct | cagaacctct | gcataatgtt | caggttttaa | 540 |
| atcaaatgat | aacatcaaaa | tcaaatccag | gaaataacat | ggcctgcatt | tctaagaatc | 600 |
| agggttcaga | gctttctgga | gtgatatctt | cagcttgtga | taagagtca | aatatggaac | 660 |
| gaagagtgat | cacgatttct | aaatcagaat | attctgtgca | ctcatctttg | gcatccaaag | 720 |
| ttgatgttga | gcaggttgtt | atgtattgca | aggagaagct | tattcgtggg | gaatcagaat | 780 |
| tttcctttga | agaattgaga | gcccagaaat | acaatcaacg | gagaaagcat | gagcaatggg | 840 |
| taaatgaaga | cagacattat | atgaaaagga | agaagcaaa | tgcttttgaa | gaacagctat | 900 |
| taaaacagaa | aatggatgaa | cttcataaga | agttgcatca | ggtggtggag | acatcccatg | 960 |
| aggatctgcc | cgcttcccag | gaaaggtccg | aggttaatcc | agcacgtatg | gggccaagtg | 1020 |
| taggctccca | gcaggaactg | agagcgccat | gtcttccagt | aacctatcag | cagacaccag | 1080 |
| tgaacatgga | aaagaaccca | agagaggcac | ctcctgttgt | tcctccttttg | gcaaatgcta | 1140 |
| tttctgcagc | tttggtgtcc | ccagccacca | gccagagcat | tgctcctcct | gttcctttga | 1200 |
| agcccagac | agtaacagac | tccatgtttg | cagtggccag | caaagatgct | ggatgtgtga | 1260 |
| ataagagtac | tcatgaattc | aagccacaga | gtggagcaga | gatcaaagaa | gggtgtgaaa | 1320 |
| cacataaggt | tgccaacaca | agttcttttc | acacaactcc | aaacacatca | ctgggaatgg | 1380 |
| ttcaggcaac | gccatccaaa | gtgcagccat | cacccaccgt | gcacacaaaa | gaagcattag | 1440 |
| gtttcatcat | gaatatgttt | caggctccta | cacttcctga | tatttctgat | gacaaagatg | 1500 |
| aatggcaatc | tctagatcaa | aatgaagatg | catttgaagc | ccagtttcaa | aaaaatgtaa | 1560 |
| ggtcatctgg | ggcttgggga | gtcaataaga | tcatctcttc | tttgtcatct | gcttttcatg | 1620 |
| tgtttgaaga | tggaaacaaa | gaaaattatg | gattaccaca | gcctaaaaat | aaacccacag | 1680 |
| gagccaggac | ctttggagaa | cgctctgtca | gcagacttcc | ttcaaaacca | aaggaggaag | 1740 |
| tgcctcatgc | tgaagagttt | ttggatgact | caactgtatg | gggtattcgc | tgcaacaaaa | 1800 |
| ccctggcacc | cagtcctaag | agcccaggag | acttcacatc | tgctgcacaa | cttgcgtcta | 1860 |
| caccattcca | caagcttcca | gtggagtcag | tgcacatttt | agaagataaa | gaaatgtgg | 1920 |
| tagcaaaaca | gtgtacccag | gcgactttgg | attcttgtga | ggaaaacatg | gtggtgcctt | 1980 |
| caagggatgg | aaaattcagt | ccaattcaag | agaaaagccc | aaaacaggcc | ttgtcgtctc | 2040 |

-continued

```
acatgtattc agcatcctta cttcgtctga gccagcctgc tgcaggtggg gtacttacct      2100
gtgaggcaga gttgggcgtt gaggcttgca gactcacaga cactgacgct gccattgcag      2160
aagatccacc agatgctatt gctgggctcc aagcagaatg gatgcagatg agttcacttg      2220
ggactgttga tgctccaaac ttcattgttg ggaacccatg ggatgataag ctgattttca      2280
aacttttatc tgggctttct aaaccagtga gttcctatcc aaatactttt gaatggcaat      2340
gtaaacttcc agccatcaag cccaagactg aatttcaatt gggttctaag ctggtctatg      2400
tccatcacct tcttggagaa ggagcctttg cccaggtgta cgaagctacc cagggagatc      2460
tgaatgatgc taaaaataaa cagaaatttg ttttaaaggt ccaaaagcct gccaaccect      2520 gggaattcta cattgggacc cagttgatgg aaagactaaa gccatctatg cagcacatgt      2580
ttatgaagtt ctattctgcc cacttattcc agaatggcag tgtattagta ggagagctct      2640
acagctatgg aacattatta aatgccatta acctctataa aaatacccct gaaaaagtga      2700
tgcctcaagg tcttgtcatc tcttttgcta tgagaatgct ttacatgatt gagcaagtgc      2760
atgactgtga aatcattcat ggagacatta accagacaa tttcatactt ggaaacggat       2820
ttttggaaca ggatgatgaa atgatttat ctgctggctt ggcactgatt gacctgggtc       2880
agagtataga tatgaaactt tttccaaaag gaactatatt cacagcaaag tgtgaaacat      2940
ctggttttca gtgtgttgag atgctcagca acaaaccatg gaactaccag atcgattact      3000 ttgggggttgc tgcaacagta tattgcatgc tctttggcac ttacatgaaa gtgaaaaatg     3060
aaggaggaga gtgtaagcct gaaggtcttt ttagaaggct tcctcatttg gatatgtgga     3120 atgaatttt tcatgttatg ttgaatattc cagattgtca tcatcttcca tctttggatt      3180
tgttaaggca aaagctgaag aaagtatttc aacaacacta tactaacaag attagggccc     3240
tacgtaatag gctaattgta ctgctcttag aatgtaagcg ttcacgaaaa taaaatttgg     3300
atatagacag tccttaaaaa tcacactgta aatatgaatc tgctcacttt aaacctgttt     3360 tttttcatt tattgtttat gtaaatgttt gttaaaaata aatcccatgg aatatttcca      3420
tgtaaaaaaa aaaaaaaaaa a                                                3441
```

<210> SEQ ID NO 2
<211> LENGTH: 1085
<212> TYPE: PRT
<213> ORGANISM: Homo sapien

<400> SEQUENCE: 2

```
Met Asp Thr Pro Glu Asn Val Leu Gln Met Leu Glu Ala His Met Gln
  1               5                  10                  15

Ser Tyr Lys Gly Asn Asp Pro Leu Gly Glu Trp Glu Arg Tyr Ile Gln
                 20                  25                  30

Trp Val Glu Glu Asn Phe Pro Glu Asn Lys Glu Tyr Leu Ile Thr Leu
             35                  40                  45

Leu Glu His Leu Met Lys Glu Phe Leu Asp Lys Lys Tyr His Asn
         50                  55                  60

Asp Pro Arg Phe Ile Ser Tyr Cys Leu Lys Phe Ala Glu Tyr Asn Ser
 65                  70                  75                  80

Asp Leu His Gln Phe Phe Glu Phe Leu Tyr Asn His Gly Ile Gly Thr
                 85                  90                  95

Leu Ser Ser Pro Leu Tyr Ile Ala Trp Ala Gly His Leu Glu Ala Gln
                100                 105                 110

Gly Glu Leu Gln His Ala Ser Ala Val Leu Gln Arg Gly Ile Gln Asn
```

-continued

```
            115                 120                 125
Gln Ala Glu Pro Arg Glu Phe Leu Gln Gln Gln Tyr Arg Leu Phe Gln
    130                 135                 140
Thr Arg Leu Thr Glu Thr His Leu Pro Ala Gln Ala Arg Thr Ser Glu
145                 150                 155                 160
Pro Leu His Asn Val Gln Val Leu Asn Gln Met Ile Thr Ser Lys Ser
                165                 170                 175
Asn Pro Gly Asn Asn Met Ala Cys Ile Ser Lys Asn Gln Gly Ser Glu
            180                 185                 190
Leu Ser Gly Val Ile Ser Ser Ala Cys Asp Lys Glu Ser Asn Met Glu
        195                 200                 205
Arg Arg Val Ile Thr Ile Ser Lys Ser Glu Tyr Ser Val His Ser Ser
210                 215                 220
Leu Ala Ser Lys Val Asp Val Glu Gln Val Val Met Tyr Cys Lys Glu
225                 230                 235                 240
Lys Leu Ile Arg Gly Glu Ser Glu Phe Ser Phe Glu Glu Leu Arg Ala
                245                 250                 255
Gln Lys Tyr Asn Gln Arg Arg Lys His Glu Gln Trp Val Asn Glu Asp
            260                 265                 270
Arg His Tyr Met Lys Arg Lys Glu Ala Asn Ala Phe Glu Glu Gln Leu
        275                 280                 285
Leu Lys Gln Lys Met Asp Glu Leu His Lys Lys Leu His Gln Val Val
    290                 295                 300
Glu Thr Ser His Glu Asp Leu Pro Ala Ser Gln Glu Arg Ser Glu Val
305                 310                 315                 320
Asn Pro Ala Arg Met Gly Pro Ser Val Gly Ser Gln Gln Glu Leu Arg
                325                 330                 335
Ala Pro Cys Leu Pro Val Thr Tyr Gln Gln Thr Pro Val Asn Met Glu
            340                 345                 350
Lys Asn Pro Arg Glu Ala Pro Val Val Pro Leu Ala Asn Ala
        355                 360                 365
Ile Ser Ala Ala Leu Val Ser Pro Ala Thr Ser Gln Ser Ile Ala Pro
    370                 375                 380
Pro Val Pro Leu Lys Ala Gln Thr Val Thr Asp Ser Met Phe Ala Val
385                 390                 395                 400
Ala Ser Lys Asp Ala Gly Cys Val Asn Lys Ser Thr His Glu Phe Lys
                405                 410                 415
Pro Gln Ser Gly Ala Glu Ile Lys Glu Gly Cys Glu Thr His Lys Val
            420                 425                 430
Ala Asn Thr Ser Ser Phe His Thr Thr Pro Asn Thr Ser Leu Gly Met
        435                 440                 445
Val Gln Ala Thr Pro Ser Lys Val Gln Pro Ser Pro Thr Val His Thr
    450                 455                 460
Lys Glu Ala Leu Gly Phe Ile Met Asn Met Phe Gln Ala Pro Thr Leu
465                 470                 475                 480
Pro Asp Ile Ser Asp Asp Lys Asp Glu Trp Gln Ser Leu Asp Gln Asn
                485                 490                 495
Glu Asp Ala Phe Glu Ala Gln Phe Gln Lys Asn Val Arg Ser Ser Gly
            500                 505                 510
Ala Trp Gly Val Asn Lys Ile Ile Ser Ser Leu Ser Ser Ala Phe His
        515                 520                 525
Val Phe Glu Asp Gly Asn Lys Glu Asn Tyr Gly Leu Pro Gln Pro Lys
    530                 535                 540
```

-continued

Asn Lys Pro Thr Gly Ala Arg Thr Phe Gly Glu Arg Ser Val Ser Arg
545                 550                 555                 560

Leu Pro Ser Lys Pro Lys Glu Val Pro His Ala Glu Glu Phe Leu
            565                 570                 575

Asp Asp Ser Thr Val Trp Gly Ile Arg Cys Asn Lys Thr Leu Ala Pro
                580                 585                 590

Ser Pro Lys Ser Pro Gly Asp Phe Thr Ser Ala Ala Gln Leu Ala Ser
            595                 600                 605

Thr Pro Phe His Lys Leu Pro Val Glu Ser Val His Ile Leu Glu Asp
            610                 615                 620

Lys Glu Asn Val Val Ala Lys Gln Cys Thr Gln Ala Thr Leu Asp Ser
625                 630                 635                 640

Cys Glu Glu Asn Met Val Val Pro Ser Arg Asp Gly Lys Phe Ser Pro
                645                 650                 655

Ile Gln Glu Lys Ser Pro Lys Gln Ala Leu Ser Ser His Met Tyr Ser
            660                 665                 670

Ala Ser Leu Leu Arg Leu Ser Gln Pro Ala Ala Gly Gly Val Leu Thr
            675                 680                 685

Cys Glu Ala Glu Leu Gly Val Glu Ala Cys Arg Leu Thr Asp Thr Asp
690                 695                 700

Ala Ala Ile Ala Glu Asp Pro Pro Asp Ala Ile Ala Gly Leu Gln Ala
705                 710                 715                 720

Glu Trp Met Gln Met Ser Ser Leu Gly Thr Val Asp Ala Pro Asn Phe
                725                 730                 735

Ile Val Gly Asn Pro Trp Asp Asp Lys Leu Ile Phe Lys Leu Leu Ser
                740                 745                 750

Gly Leu Ser Lys Pro Val Ser Ser Tyr Pro Asn Thr Phe Glu Trp Gln
            755                 760                 765

Cys Lys Leu Pro Ala Ile Lys Pro Lys Thr Glu Phe Gln Leu Gly Ser
770                 775                 780

Lys Leu Val Tyr Val His His Leu Leu Gly Glu Gly Ala Phe Ala Gln
785                 790                 795                 800

Val Tyr Glu Ala Thr Gln Gly Asp Leu Asn Asp Ala Lys Asn Lys Gln
                805                 810                 815

Lys Phe Val Leu Lys Val Gln Lys Pro Ala Asn Pro Trp Glu Phe Tyr
            820                 825                 830

Ile Gly Thr Gln Leu Met Glu Arg Leu Lys Pro Ser Met Gln His Met
            835                 840                 845

Phe Met Lys Phe Tyr Ser Ala His Leu Phe Gln Asn Gly Ser Val Leu
850                 855                 860

Val Gly Glu Leu Tyr Ser Tyr Gly Thr Leu Leu Asn Ala Ile Asn Leu
865                 870                 875                 880

Tyr Lys Asn Thr Pro Glu Lys Val Met Pro Gln Gly Leu Val Ile Ser
            885                 890                 895

Phe Ala Met Arg Met Leu Tyr Met Ile Glu Gln Val His Asp Cys Glu
            900                 905                 910

Ile Ile His Gly Asp Ile Lys Pro Asp Asn Phe Ile Leu Gly Asn Gly
            915                 920                 925

Phe Leu Glu Gln Asp Glu Asp Leu Ser Ala Gly Leu Ala Leu
            930                 935                 940

Ile Asp Leu Gly Gln Ser Ile Asp Met Lys Leu Phe Pro Lys Gly Thr
945                 950                 955                 960

-continued

```
Ile Phe Thr Ala Lys Cys Glu Thr Ser Gly Phe Gln Cys Val Glu Met
                965                 970                 975
Leu Ser Asn Lys Pro Trp Asn Tyr Gln Ile Asp Tyr Phe Gly Val Ala
            980                 985                 990
Ala Thr Val Tyr Cys Met Leu Phe Gly Thr Tyr Met Lys Val Lys Asn
        995                1000                1005
Glu Gly Gly Glu Cys Lys Pro Glu Gly Leu Phe Arg Arg Leu Pro His
    1010                1015                1020
Leu Asp Met Trp Asn Glu Phe His Val Met Leu Asn Ile Pro Asp
1025                1030                1035                1040
Cys His His Leu Pro Ser Leu Asp Leu Arg Gln Lys Leu Lys Lys
                1045                1050                1055
Val Phe Gln Gln His Tyr Thr Asn Lys Ile Arg Ala Leu Arg Asn Arg
                1060                1065                1070
Leu Ile Val Leu Leu Leu Glu Cys Lys Arg Ser Arg Lys
            1075                1080                1085

<210> SEQ ID NO 3
<211> LENGTH: 2619
<212> TYPE: DNA
<213> ORGANISM: Homo sapien

<400> SEQUENCE: 3
gaagcaagga ggcggcggcg gccgagcgag tggcgagtag tggaaacgtt gcttctgagg      60
ggagcccaag atgaccggtt ctaacgagtt caagctgaac cagccacccg aggatggcat     120
ctcctccgtg aagttcagcc ccaacaccctc ccagttcctg cttgtctcct cctgggacac     180
gtccgtgcgt ctctacgatg tgccggccaa ctccatgcgg ctcaagtacc agcacaccgg     240
cgccgtcctg gactgcgcct tctacgatcc aacgcatgcc tggagtggag gactagatca     300
tcaattgaaa atgcatgatt tgaacactga tcaagaaaat cttgttggga cccatgatgc     360
ccctatcaga tgtgttgaat actgtccaga agtgaatgtg atggtcactg gaagttggga     420
tcagacagtt aaactgtggg atcccagaac tccttgtaat gctgggacct tctctcagcc     480
tgaaaaggta taccctctca gtgtctgga gaccggctga ttgtgggaa cagcaggccg     540
cagagtgttg gtgtgggact acggaacat gggttacgtg cagcagcgca gggagtccag     600
cctgaaatac cagactcgct gcatacgagc gtttccaaac aagcagggtt atgtattaag     660
ctctattgaa ggccgagtgg cagttgagta ttttggaccca agccctgagg tacagaagaa     720
gaagtatgcc ttcaaatgtc acagactaaa agaaaataat attgagcaga tttacccagt     780
caatgccatt tcttttcaca atatccacaa tacatttgcc acaggtggtt ctgatggctt     840
tgtaaatatt tgggatccat ttaacaaaaa gcgactgtgc caattccatc ggtaccccac     900
gagcatcgca tcacttgcct tcagtaatga tgggactacg cttgcaatag cgtcatcata     960
tatgtatgaa atggatgaca cagaacatcc tgaagatggt atcttcattc gccaagtgac    1020
agatgcagaa acaaaaccca gtcaccatg tacttgacaa gatttcattt acttaagtgc    1080
catgttgatg ataataaaac aattcgtact ccccaatggt ggatttatta ctattaaaga    1140
aaccagggaa atattaattt taatattat acaacctga aaataatgga aaagaggttt    1200
ttgaatttt ttttttaaat aaacaccttc ttaagtgcat gagatggttt gatggtttgc    1260
tgcattaaag gtatttgggc aaacaaaatt ggagggcaag tgactgcagt tttgagaatc    1320
agttttgacc ttgatgattt tttgtttcca ctgtggaaat aaatgtttgt aaataagtgt    1380
aataaaaatc cctttgcatt ctttctggac cttaaatggt agaggaaaag gctcgtgagc    1440
```

-continued

```
catttgtttc ttttgctggt tatagttgct aattctaaag ctgcttcaga ctgcttcatg    1500
aggaggttaa tctacaatta aacaatattt cctcttggcc gtccattatt ttctgaagca    1560
gatggttcat catttcctgg gctgttaaac aaagcgaggt taaggttaga ctcttgggaa    1620
tcagctagtt ttcaatctta ttagggtgca gaaggaaaac taataagaaa acctcctaat    1680
atcattttgt gactgtaaac aattatttat tagcaaacaa ttgatcccag aagggcaaat    1740
tgtttgagtc agtaatgagc tgagaaaaga cagagcatat ctgtgtattt ggaaaaataa    1800
ttgtaacgta attgcagtgc atttagacag gcatctattt ggacctgttt ctatctctaa    1860
atgaattttt ggaaacatta atgaggttta catatttctc tgacatttat atagttctta    1920
tgtccatttc agttgaccag ccgctggtga ttaaagttaa aaagaaaaaa attatagtga    1980
gaatgagatt catttcaatg taatgcacta agcagaaca cgaacttagc ttggcctatt    2040
ctaggtagtt ccaaatagta ttttgttgt caaactttaa aatttatatt aatttgcaaa    2100
tgtatgtctc tgagtaggac ttggaccttt cctgagattt attttatccg tgatgtattt    2160
tttttaattc ttttgataca gagaagggtc ttttttttt taagtatttc agtgaaaact    2220
tggtgtaagt ctgaacccat cttttgaaat gtattttctt cattgcaggt ccacctaatc    2280
atcctgtgaa agtggtttct ctatggaaag ctttgtttgc ttcctacaaa tacatgctta    2340
ttccttaagg gatgtgttag agttactgtg gatttctctg ttttctgtct tacaagaaac    2400
ttgtctatgt accttaatac tttgtttagg atgaggagtc tttgtgtccc tgtacagtag    2460
tctgacgtat ttccccttct gtcccctagt aagcccagtt gctgtatctg aacagtttga    2520 gctcttttg taatatactc taaacctgtt atttctgtgc taataaacga gatgcagaac    2580
ccttgaaaaa aaaaaaaaaa aaaaaaaaaa aaaaaaaa                           2619
```

<210> SEQ ID NO 4
<211> LENGTH: 328
<212> TYPE: PRT
<213> ORGANISM: Homo sapien

<400> SEQUENCE: 4

```
Met Thr Gly Ser Asn Glu Phe Lys Leu Asn Gln Pro Pro Glu Asp Gly
  1               5                  10                  15

Ile Ser Ser Val Lys Phe Ser Pro Asn Thr Ser Gln Phe Leu Leu Val
                 20                  25                  30

Ser Ser Trp Asp Thr Ser Val Arg Leu Tyr Asp Val Pro Ala Asn Ser
             35                  40                  45

Met Arg Leu Lys Tyr Gln His Thr Gly Ala Val Leu Asp Cys Ala Phe
         50                  55                  60

Tyr Asp Pro Thr His Ala Trp Ser Gly Gly Leu Asp His Gln Leu Lys
 65                  70                  75                  80

Met His Asp Leu Asn Thr Asp Gln Glu Asn Leu Val Gly Thr His Asp
                 85                  90                  95

Ala Pro Ile Arg Cys Val Glu Tyr Cys Pro Glu Val Asn Val Met Val
                100                 105                 110

Thr Gly Ser Trp Asp Gln Thr Val Lys Leu Trp Asp Pro Arg Thr Pro
            115                 120                 125

Cys Asn Ala Gly Thr Phe Ser Gln Pro Glu Lys Val Tyr Thr Leu Ser
        130                 135                 140

Val Ser Gly Asp Arg Leu Ile Val Gly Thr Ala Gly Arg Arg Val Leu
145                 150                 155                 160
```

-continued

```
Val Trp Asp Leu Arg Asn Met Gly Tyr Val Gln Gln Arg Arg Glu Ser
                165                 170                 175
Ser Leu Lys Tyr Gln Thr Arg Cys Ile Arg Ala Phe Pro Asn Lys Gln
            180                 185                 190
Gly Tyr Val Leu Ser Ser Ile Glu Gly Arg Val Ala Val Glu Tyr Leu
        195                 200                 205
Asp Pro Ser Pro Glu Val Gln Lys Lys Tyr Ala Phe Lys Cys His
    210                 215                 220
Arg Leu Lys Glu Asn Asn Ile Glu Gln Ile Tyr Pro Val Asn Ala Ile
225                 230                 235                 240
Ser Phe His Asn Ile His Asn Thr Phe Ala Thr Gly Gly Ser Asp Gly
                245                 250                 255
Phe Val Asn Ile Trp Asp Pro Phe Asn Lys Lys Arg Leu Cys Gln Phe
            260                 265                 270
His Arg Tyr Pro Thr Ser Ile Ala Ser Leu Ala Phe Ser Asn Asp Gly
        275                 280                 285
Thr Thr Leu Ala Ile Ala Ser Ser Tyr Met Tyr Glu Met Asp Asp Thr
    290                 295                 300
Glu His Pro Glu Asp Gly Ile Phe Ile Arg Gln Val Thr Asp Ala Glu
305                 310                 315                 320
Thr Lys Pro Lys Ser Pro Cys Thr
                325

<210> SEQ ID NO 5
<211> LENGTH: 23
<212> TYPE: DNA
<213> ORGANISM: Artificial Sequence
<220> FEATURE:
<223> OTHER INFORMATION: Primer for PCR amplification of huBUB1

<400> SEQUENCE: 5
atcattcatg gagacattaa gcc                                            23

<210> SEQ ID NO 6
<211> LENGTH: 24
<212> TYPE: DNA
<213> ORGANISM: Artificial Sequence
<220> FEATURE:
<223> OTHER INFORMATION: Primer for PCR amplification of huBUB1

<400> SEQUENCE: 6
tttcatgtaa gagccaaaga gcat                                           24

<210> SEQ ID NO 7
<211> LENGTH: 5
<212> TYPE: PRT
<213> ORGANISM: Homo sapien

<400> SEQUENCE: 7

Val Leu Lys Gln Val
1               5

<210> SEQ ID NO 8
<211> LENGTH: 7
<212> TYPE: PRT
<213> ORGANISM: Homo sapien

<400> SEQUENCE: 8

Arg Val Ile Thr Ile Ser Lys
1               5
```

-continued

```
<210> SEQ ID NO 9
<211> LENGTH: 44
<212> TYPE: PRT
<213> ORGANISM: S. cerevisiae

<400> SEQUENCE: 9

Asp Leu Tyr Cys Ile Arg Gly Glu Leu Gly Glu Gly Tyr Ala Thr
1               5                   10                  15

Val Tyr Leu Ala Glu Ser Ser Gln Gly His Leu Arg Ala Leu Lys Val
            20                  25                  30

Glu Lys Pro Ala Ser Val Trp Glu Tyr Tyr Ile Met
        35                  40

<210> SEQ ID NO 10
<211> LENGTH: 49
<212> TYPE: PRT
<213> ORGANISM: Mus musculus

<400> SEQUENCE: 10

Leu Val Tyr Val Asn His Leu Leu Gly Glu Gly Ala Phe Ala Gln Val
1               5                   10                  15

Phe Glu Ala Ile His Gly Asp Val Arg Asn Ala Lys Ser Glu Gln Lys
            20                  25                  30

Cys Ile Leu Lys Val Gln Arg Pro Ala Asn Ser Trp Glu Phe Tyr Ile
        35                  40                  45

Gly

<210> SEQ ID NO 11
<211> LENGTH: 49
<212> TYPE: PRT
<213> ORGANISM: Homo sapien

<400> SEQUENCE: 11

Leu Val Tyr Val His His Leu Leu Gly Glu Gly Ala Phe Ala Gln Val
1               5                   10                  15

Tyr Glu Ala Thr Gln Gly Asp Leu Asn Asp Ala Lys Asn Lys Gln Lys
            20                  25                  30

Phe Val Leu Lys Val Gln Lys Pro Ala Asn Pro Trp Glu Phe Tyr Ile
        35                  40                  45

Gly

<210> SEQ ID NO 12
<211> LENGTH: 46
<212> TYPE: PRT
<213> ORGANISM: Homo sapien

<400> SEQUENCE: 12

Thr Asp Phe Asn Phe Leu Met Val Leu Gly Lys Gly Ser Phe Gly Lys
1               5                   10                  15

Val Met Leu Ala Asp Arg Lys Gly Thr Glu Glu Leu Tyr Ala Ile Lys
            20                  25                  30

Ile Leu Lys Lys Asp Val Val Ile Gln Asp Asp Val Glu
        35                  40                  45

<210> SEQ ID NO 13
<211> LENGTH: 49
<212> TYPE: PRT
<213> ORGANISM: Homo sapien

<400> SEQUENCE: 13
```

```
Glu Cys Phe Glu Leu Leu Arg Val Leu Gly Lys Gly Gly Tyr Gly Lys
 1               5                  10                 15

Val Phe Gln Val Arg Lys Val Thr Gly Ala Asn Thr Gly Lys Ile Phe
            20                  25                  30

Ala Met Lys Val Leu Lys Lys Ala Met Ile Val Arg Asn Ala Lys Asp
        35                  40                  45

Thr

<210> SEQ ID NO 14
<211> LENGTH: 46
<212> TYPE: PRT
<213> ORGANISM: Homo sapien

<400> SEQUENCE: 14

Asp Gln Phe Glu Arg Ile Lys Thr Leu Gly Thr Gly Ser Phe Gly Arg
 1               5                  10                 15

Val Met Leu Val Lys His Lys Glu Thr Gly Asn His Tyr Ala Met Lys
            20                  25                  30

Ile Leu Asp Lys Gln Lys Val Val Lys Leu Lys Gln Ile Glu
        35                  40                  45

<210> SEQ ID NO 15
<211> LENGTH: 44
<212> TYPE: PRT
<213> ORGANISM: Homo sapien

<400> SEQUENCE: 15

Val Ser Tyr Thr Asp Thr Lys Val Ile Gly Asn Gly Ser Phe Gly Val
 1               5                  10                 15

Val Tyr Gln Ala Lys Leu Cys Asp Ser Gly Glu Leu Val Ala Ile Lys
            20                  25                  30

Lys Val Leu Gln Asp Lys Arg Phe Lys Asn Arg Glu
        35                  40
```